(12) United States Patent
Henderson et al.

(10) Patent No.: US 6,998,228 B2
(45) Date of Patent: Feb. 14, 2006

(54) METHOD AND APPARATUS FOR SOLID STATE MOLECULAR ANALYSIS

(75) Inventors: Eric Henderson, Ames, IA (US); Curtis Mosher, Ames, IA (US); Michael P. Lynch, Ames, IA (US)

(73) Assignee: Bioforce Nanosciences, Inc., Ames, IA (US)

( * ) Notice: Subject to any disclaimer, the term of this patent is extended or adjusted under 35 U.S.C. 154(b) by 575 days.

(21) Appl. No.: 10/179,102

(22) Filed: Jun. 25, 2002

(65) Prior Publication Data

US 2003/0013111 A1 Jan. 16, 2003

Related U.S. Application Data

(62) Division of application No. 09/574,519, filed on May 18, 2000, now Pat. No. 6,573,369.
(60) Provisional application No. 60/135,290, filed on May 21, 1999.

(51) Int. Cl.
C12Q 1/68 (2006.01)

(52) U.S. Cl. .................................. 435/4; 435/6; 435/7.1
(58) Field of Classification Search .................... 435/4, 435/6, 7.1
See application file for complete search history.

(56) References Cited

U.S. PATENT DOCUMENTS

| | | |
|---|---|---|
| 4,728,591 A | 3/1988 | Clark et al. |
| 5,106,729 A | 4/1992 | Lindsay et al. |
| 5,138,174 A | 8/1992 | Tang ........................ 250/492.3 |
| 5,143,854 A | 9/1992 | Pirrung et al. |
| 5,314,829 A | 5/1994 | Coles |
| 5,346,683 A | 9/1994 | Green et al. |
| 5,363,697 A | 11/1994 | Nakagawa |
| 5,372,930 A | 12/1994 | Colton et al. |
| 5,384,261 A | 1/1995 | Winkler et al. |
| 5,440,122 A | 8/1995 | Yasutake |
| 5,443,791 A | 8/1995 | Cathcart et al. |
| 5,445,934 A | 8/1995 | Fodor et al. |
| 5,445,971 A | 8/1995 | Rohr |
| 5,453,970 A | 9/1995 | Rust et al. |
| 5,467,642 A | 11/1995 | Hosaka et al. |
| 5,472,881 A | 12/1995 | Beebe et al. |
| 5,482,601 A | 1/1996 | Ohshima et al. |
| 5,514,540 A | 5/1996 | Teoule et al. |
| 5,514,550 A | 5/1996 | Findlay et al. |
| 5,519,212 A | 5/1996 | Elings et al. |
| 5,532,128 A | 7/1996 | Eggers et al. |
| 5,571,639 A | 11/1996 | Hubbell et al. |
| 5,601,982 A | 2/1997 | Sargent et al. |
| 5,604,097 A | 2/1997 | Brenner |
| 5,620,854 A | 4/1997 | Holzrichter et al. |
| 5,666,190 A | 9/1997 | Quate et al. |
| 5,670,322 A | 9/1997 | Eggers et al. |
| 5,688,486 A | 11/1997 | Watson et al. |
| 5,720,928 A | 2/1998 | Schwartz |
| 5,744,305 A | 4/1998 | Fodor et al. |

(Continued)

FOREIGN PATENT DOCUMENTS

| | | |
|---|---|---|
| JP | 06124680 | 5/1994 |
| JP | 07027771 | 1/1995 |
| JP | 08094646 | 4/1996 |
| WO | WO 92/15709 | 9/1992 |
| WO | WO 9631775 | of 1996 |

(Continued)

OTHER PUBLICATIONS

"Microbeam Mass Spectrometry" *Chemical Science and Technology Laboratory, Surface and Microanalysis Science Division* http://www.cstl.nist.gov/div837/Divisoin/expertise/ions/masspec1.htm Jul. 18, 2002.

Abstracts of Papers Part I, $214^{th}$ "Abstract 027" *ACS National Meeting American Chemical Society*, Sep. 1997, 2 pgs.

Allison, D., et al., "Direct atomic force microscopy imaging of *EcoRI* endonuclease site specifically bound to plasmid DNA molecules" *PNAS USA*, 1996, 93:8826–8829.

Allison, D., et al., "Mapping Individual Cosmid DNAs by Direct AFM Imaging" *Genomcis*, 1997, 41:379–384.

Alves, et al., Atomic scale imaging of alkanethiolate monolayers at gold surfaces with atomic force microscopy: *J. Am. Chem. Soc.*, Feb. 1992,114(4):1222–1227.

Amro, et al., "Patterning surfaces using tip–directed displacement and self–assembly" *Langmuir*, 2000, 16:3006–3009.

(Continued)

*Primary Examiner*—Jeffrey Fredman
(74) *Attorney, Agent, or Firm*—Michael Best & Friedrich, LLP

(57) ABSTRACT

The invention is a method for the formation and analysis of novel miniature deposition domains. These deposition domains are placed on a surface to form a molecular array. The molecular array is scanned with an AFM to analyze molecular recognition events and the effect of introduced agents on defined molecular interactions. This approach can be carried out in a high throughput format, allowing rapid screening of thousands of molecular species in a solid state array. The procedures described here have the added benefit of allowing the measurement of changes in molecular binding events resulting from changes in the analysis environment or introduction of additional effector molecules to the assay system. The processes described herein are extremely useful in the search for compounds such as new drugs for treatment of undesirable physiological conditions. The method and apparatus of the present invention does not require the labeling of the deposition material or the target sample and may also be used to deposit large size molecules without harming the same.

44 Claims, 7 Drawing Sheets

U.S. PATENT DOCUMENTS

| | | |
|---|---|---|
| 5,753,088 A | 5/1998 | Olk |
| 5,760,300 A | 6/1998 | Kajimura |
| 5,763,768 A | 6/1998 | Henderson et al. |
| 5,789,167 A | 8/1998 | Konrad |
| 5,800,992 A | 9/1998 | Fodor et al. |
| 5,837,832 A | 11/1998 | Chee et al. |
| 5,840,862 A | 11/1998 | Bensimon et al. |
| 5,846,724 A | 12/1998 | Bensimon et al. |
| 5,851,769 A | 12/1998 | Gray et al. |
| 5,866,328 A | 2/1999 | Bensimon et al. |
| 5,866,434 A | 2/1999 | Massey et al. |
| 5,874,219 A | 2/1999 | Rava et al. |
| 5,874,668 A | 2/1999 | Xu et al. |
| 5,958,701 A | 9/1999 | Green et al. |
| 5,965,133 A | 10/1999 | Cantor et al. |
| 5,981,733 A | 11/1999 | Gamble et al. |
| 5,985,356 A | 11/1999 | Schultz et al. |
| 5,992,226 A | 11/1999 | Green et al. |
| 5,993,627 A | 11/1999 | Anderson et al. |
| 6,004,617 A | 12/1999 | Schultz et al. |
| 6,024,925 A | 2/2000 | Little et al. |
| 6,033,911 A | 3/2000 | Schultz et al. |
| 6,045,671 A | 4/2000 | Wu et al. |
| 6,080,586 A | 6/2000 | Baldeschwieler et al. |
| 6,083,763 A | 7/2000 | Balch |
| 6,087,274 A | 7/2000 | Tonucci et al. |
| 6,110,426 A | 8/2000 | Shalon et al. |
| 6,123,819 A | 9/2000 | Peeters |
| 6,143,574 A | 11/2000 | Karlsson et al. |
| 6,146,899 A | 11/2000 | Porter et al. |
| 6,159,742 A | 12/2000 | Lieber et al. |
| 6,171,797 B1 | 1/2001 | Perbost |
| 6,180,114 B1 | 1/2001 | Yager |
| 6,200,737 B1 | 3/2001 | Walt et al. |
| 6,203,814 B1 | 3/2001 | Fisher et al. |
| 6,214,552 B1 | 4/2001 | Heroux et al. |
| 6,218,122 B1 | 4/2001 | Friend et al. |
| 6,231,744 B1 | 5/2001 | Ying et al. |
| 6,232,706 B1 | 5/2001 | Dai et al. |
| 6,239,273 B1 | 5/2001 | Pease et al. |
| 6,255,469 B1 | 7/2001 | Seeman et al. |
| 6,270,946 B1 | 8/2001 | Miller |
| 6,278,231 B1 | 8/2001 | Iwasaki et al. |
| 6,284,497 B1 | 9/2001 | Sabanayagam et al. |
| 6,287,850 B1 | 9/2001 | Besemer et al. |
| 6,289,717 B1 | 9/2001 | Thundat et al. |
| 6,309,831 B1 | 10/2001 | Goldberg et al. |
| 6,329,209 B1 | 12/2001 | Wagner et al. |
| 6,331,396 B1 | 12/2001 | Silverman |
| 6,350,609 B1 | 2/2002 | Morozov et al. |
| 6,395,554 B1 | 5/2002 | Regan et al. |
| 6,406,921 B1 | 6/2002 | Wagner et al. |
| 6,416,952 B1 | 7/2002 | Pirrung et al. |
| 6,420,105 B1 | 7/2002 | Landfield et al. |
| 6,436,647 B1 | 8/2002 | Quate et al. |
| 6,518,168 B1 | 2/2003 | Clem et al. |
| 6,573,369 B1 | 6/2003 | Henderson et al. |
| 2002/0042081 A1 | 4/2002 | Henderson et al. |
| 2002/0063212 A1 | 5/2002 | Mirkin et al. |
| 2002/0076927 A1 | 6/2002 | Henderson et al. |
| 2002/0114987 A1 | 8/2002 | Oscarsson et al. |
| 2002/0122873 A1 | 9/2002 | Mirkin et al. |
| 2002/0123135 A1 | 9/2002 | Henderson et al. |
| 2002/0146714 A1 | 10/2002 | Lieber et al. |
| 2002/0172943 A1 | 11/2002 | Henderson et al. |
| 2002/0179434 A1 | 12/2002 | Dai et al. |
| 2003/0013111 A1 | 1/2003 | Henderson et al. |

FOREIGN PATENT DOCUMENTS

| | | |
|---|---|---|
| WO | WO 96/31775 | 10/1996 |
| WO | WO 97/06420 | 2/1997 |
| WO | WO 97/18326 | 5/1997 |
| WO | WO 98/05920 | 2/1998 |
| WO | WO 98/18959 | 5/1998 |
| WO | WO 99/31267 | 6/1999 |
| WO | WO 00/04382 | 1/2000 |
| WO | WO 00/04382 A1 | 1/2000 |
| WO | WO 00/04389 | 1/2000 |
| WO | WO 00/04390 | 1/2000 |
| WO | WO 00/36136 | 6/2000 |
| WO | WO 00/41213 | 7/2000 |
| WO | WO 00/46406 | 8/2000 |
| WO | WO 01/60316 | 8/2001 |
| WO | WO 01/918555 | 12/2001 |
| WO | WO 03/001633 | 1/2003 |
| WO | WO 03/036767 | 5/2003 |
| WO | WO 03/038033 | 5/2003 |
| WO | WO 03/048314 | 6/2003 |
| WO | WO 03/052514 | 6/2003 |

OTHER PUBLICATIONS

Anwander, et al., "Surface characterization and functionalization of MCM–41 silicas via silazane silylation" *J. Phys. Chem. B.,* 2000, 104:3532–3544.

Arntz, et al., "Label–free protein assay based on a nanomechanical cantilever array" *Nanotechnology,* 14 (2003) 86–90.

Ausubel, F.M., et al. "Current Protocols in Molecular Biology" 1993 ed. vol. 1&2, 1993, Green Publishing Associates and Wiley–Interscience.

Avouris, P., et al., "Engineering Carbon Nanotubes and Nanotube Circuits Using Electrical Breakdown" *Science,* Apr. 2001, 292(5517):706–799.

Bailey, C.P., et al., Cationic oligonucleotides can mediate specific inhibition of gene expression in Xenopus oocytes *Nuc. Acids Res.,* 1998, 26(21):4860–4867.

Bain, et al., "Modeling organic surfaces with self–assembled monolayers" *Agnew. Chem. Int. Ed. Engl.,* 1989, 28(4):506–512.

Baselt, D.R., et al., "A biosensor based on magnetoresistance technology" *Biosens. Bioelectorn,* 1998, 13(7–8):731–739.

Bedouelle, H., "Reagentless fluorescent Immunosensors" *Antibody Engineering,* IBC's 13th International Conference, Dec. 2, 2002.

Belaubre, P. et al., "Fabrication of biological microarrays using microcantilevers" *Applied Physics Letters,.* May 5, 2003, 82(18):3122–3124.

Bensimon, A., et al., "Alignment and sensitive detection of DNA by a moving interface" *Science,* Sep. 30, 1994; 265(5181):2096–2098 [PMID 7522347] Abstract.

Berggren, et al., "Microlithography by using neutral metastable atoms and self–assembled monolayers" *Science,* Sep. 1995, 269(5228):1255–1257.

Bernard, et al. "Printing patterns of proteins" *Langmuir The ACS Journal of Surfaces and Colliod,* Apr. 1998, 14(9):2225–2229.

Binggeli, et al., "Influence of capillary condensation of water on nanotribology studied by force microscopy" *Appl. Phys. Lett.,* Jul. 1994, 65(4):415–417.

Binning, et al., "Surface studies by scanning tunneling microscopy" *Phys. Rev. Lett.,* 1982, 49(1):57–61.

Binning, G., et al., Atomic force microscope *Phys. Rev. Lett.*, 1986, 56(9):930–933.

Bishop, et al., "Self–assembled monolayers: recent developments and applications" *Colloid & Interface Science*, Feb. 1996, 1:127–136.

Bottomley, L., "Scanning probe microscopy" *Anal. Chem.*, Jun. 1998, 70(12):425R–475R.

Brandow, S., et al., "Metal pattern fabrication using the local electric field of conducting atomic force microscope probe" *J. Vac. Sci. Technol.*, May/Jun. 1997, 15(3):1455–1459.

Brenner, S., et al., "Gene expression analysis by massively parallel signature sequencing (MPSS) on microbead arrays" *Nat. Biotechnol. 2000*, Jun. 18(6):630–634, 2000.

Brody, E., and Gold, L., "Aptamers as therapeutic and diagnostic agents" *Molecular Biotechnology*, 2000, 74:5–13.

Bruckbauer, et al., "Writing with DNA and Protein Using a Nanopipet for Controlled Delivery" *JACS*, 2002, A–B.

Bulyk, et al., "Quantifying DNA–protein interactions by double–stranded DNA arrays" *Nature Biotechnology*, Jun. 1999, 17:573–577.

Bustamante C., et al., "Circular DNA Molecules Imaged in Air by Scanning Force Microscopy" *Biochemistry*, 1992, 31:22–26.

Bustamante, C., et al., "Biochemical and structural applications of scanning force microscopy" *Curr. Opin. Struct. Biol.*, 1994 4(5):750–760.

Carr, et al., "High–selectivity pattern transfer process for self–assembled monolayer electron beam resists" *J. Vac. Sci. Technol.*, May/Jun. 1997, 15(3):1446–1450.

Cheng, et al., "Preparation and hybridization analysis of DNA/RNA from *E. coli* on microfabricated bioelectronic chips" *Nature Biotechnology*, 1998, 16:541–546.

Chrisey et al, "Fabrication of patterned DNA surfaces" *Nucleic Acids Research*, (Oct. 1996)24(15):3040–3047.

Clark, M.W. et al., "Nanotechnology tools for functional proteomics analysis" *American Biotechnology Laboratory*, Mar. 2001, 16–18.

Colas, et al., "Genetic selection of peptide aptamers that recognize an inhibit cyclin–dependent kinase 2", *Nature*, Apr. 1996 380(11):548–550.

Colvin, et al. "Semiconductor nanocrystals covalently bound to metal surfaces with self–assembled monolayers" *J. Am. Chem. Soc.*, 1992, 114:5221–5230.

Cui, Y. et al., "Nanowire nanosensors for highly sensitive and selective detection of biological and chemical species" *Science*, 2001, 293, 1289–1292.

Dai, et al., "Nanotube Molecular Wires as Chemical Sensors" *Science*, Jan. 28, 2000, 287:622–625.

Dai, H, et al., "Controlled chemical routes to nanotube architectures" Physics and Devices, *J. Phys. Chem B*, 1999, 103:11246–11255.

Dai, H, et al., "Probing electrical transport in nanomaterials: conductivity of individual carbon nanotubes" *Science*, 1996, 272(5261):523–526.

Dammer, et al., "Binding strength between cell adhesion proteoglycans measured by atomic force microscopy" *Science*, 1995, 267:1173–1175.

Dammer, et al., "Specific antigen/antibody interactions measured by force microscopy" *Biophys. J.*, 1996, 70:2437–2441.

Delamarche, E., et al., "Patterned delivery of immunoglobulins to surfaces using microfluidic networks" *Science*, 1997, 276:779–781.

Ding, Y., Oka, T., et al., "Near–field stimulated TOF nanometric surface mass spectroscopy: characterization of Nano–localized surfaces" Joint International Meeting—200th Meeting of the Electrochemical Society, Inc., 52nd Annual Meeting of the International Society of Electrochemistry, San Francisco, California (2001).

Ding, Y., Ruggero, M. et al., "Development of UHV–STM/TOF hybrid mass analyzer systems for nano–characterization of metal silicide surfaces" 198th Meeting of the Electrochemical Society, Phoenix, Arizona (2000).

DeRisi, et al., "Exploring the Metabolic and Genetic Control of Gene Expression on a Genomic Scale" *Science*, Oct. 1997, 278:680–686.

Dong, Y. and Shannon, C., "Heterogeneous Immunosensing Using Antigen and Antibody Monolayers on Gold Surfaces with Electrochemical and Scanning Probe Detection" *Anal. Chem.*, 2000, 72:2371–2376.

Dontha, N., et al., "Development of sub–micron patterned carbon electrodes for immunoassay" *J. Pharm. Biomed. Analysis*, (Feb. 1999) 19:83–91.

Dontha, N., et al., "Generation of Biotin/Avidin/Enzyme Nanostructures with Maskless Photoligography" *Anal. Chem.*, 1997, 69: 619–2625.

Dubois, L. et al., "Synthesis, Structure, and Properties of Model Organic Surfaces" *Annu. Rev. Phys. Chem.*, 1992, 43:437–463.

Durbin, S., Feher, G., "Protein crystallization" *Annual Review of Phys Chemistry*, 1996, 47:171–204.

Falvo, M.R., et al., "Bending and buckling of carbon naotubes under large strain" *Nature*, 1997, 389:582–584.

Fan, S., et al., "Self–oriented regular arrays of carbon nanotubes and their functional devices" *Science*, 1999, 283, 512.

Fang, et al., "Membrane Protein Microarrays" *JACS*, 2002, 124(11):2394–2395.

Farajian, A.A., et al., "Nonlinear Coherent Transport Through Doped Nanotube Junctions" *Physical Review*, Jun. 21, 1999, 82(25):5084–5087.

Feigon, J. "DNA triplexes, quadruplexe, and aptamers" *Clin. Chem.*, 1994, 40(4):647–647.

Florin, E., et al., "Adhesion forces between individual ligan–receptor pairs" *Science*, 1994, 264:415–417.

Fodor, S., et al., "Light–directed spatially addressable parallel chemical synthesis" *Science* 1991, 251: 767–773.

Fodor, S., et al., "Multiplexed biochemical assays with biological chips" *Nature*, 1993, 364:555–557.

Frisbie, C.D., et al., "Functional group imaging by chemical force microscopy" *Science*, 1994, 265:2071–2074.

Fritz, J., et al., "Translating biomolecular recognition into nanomechanics" *Science*, 2000, 316–318.

Fritzsche, W., et al., "Application of Atomic Force Microscopy to Visualization of DNA, Chromatin and Chromosomes" *Critical Reviews™ in Eukaryotic Gene Expression*, 1997, 7(3):231–240.

Fritzsche, W., et al., "Chicken Erythrocyte Nucleosomes Have a Defined Orientation along the Linker DNA–A Scanning Force Microscopy Study" *Scanning*, 1997, 19:42–47.

Fritzsche, W., et al., "Mapping elasticity of rehydration metaphase chromosomes by scanning force microscopy" *Ultramicroscopy*, 1997, 69:191–200.

Fritsche, W., et al., "Ribosomes substructure investigated by scanning force microscopy and image processing" *Journal of Microscopy*, 1998, 189 Pt 1, 50–56.

Fujihira, et al., "Effect of capillary force on friction force microscopy: a scanning hydrophilicity microscope" *Chemistry Letters,* Jul. 1996, 7:499–500.

Gillen, G., Bennett, J., et al., "Molecular imaging secondary ion mass spectrometry for the characterization of patterned self–assembled monolayers on silver and gold" *Anal. Chemistry,* 1994, 66:2170–2174.

Girault, S., Chassaing, G. et al, "Coupling of MALDI–TOF mass analysis to the separation of biotinylated peptides by magnetic streptavidin beads" *Anal. Chemistry* 1996, 68:2122–2126.

Grabar, et al., "Preparation and characterization of Au colloid monolayers" *Anal. Chem.,* 1995, 67(4):735–743.

Haab, et al., "Protein microarrays for highly parallel detection and quantitation of specific proteins and antibodies in complex solutions" *Genome Biology,* 2001, 2(2)0004.1–0004.13.

Hansma, H.G., et al., "Atomic force microscopy of long and short double–stranded, single–stranded and triple–stranded nucleic acids" *Nuc. Acids Res.,* 1996, 24(4):713–720.

Hansma, H.G., et al., "Recent advances in atomic force microscopy of DNA" *Scanning* 1993, 15(5):296–9.

Hansma, H.G., Sinsheimer, R.L., et al., "Atomic force microscopy of single–and double–stranded DNA" *Nucleic Acids Research* 1992, 20:3585–90.

Hansma, P.K., et al., "Tapping mode atomic force microscopy in liquids" *Appl. Phys. Lett.,* 1994, 64(13):1738–1740.

Heller, et al., "Discovery and analysis of inflammatory disease–related genes using cDNA microarrays" *PNAS USA,* 1997, 94: 2150–2155.

Henderson, E., "Atomic force microscopy of conventional and unconventional nucleic acid structures" *Journal of Microscopy,* 1992, 77–84.

Henderson, E., "Imaging and nanodissection of individual supercoiled plasmids by atomic force microscopy" *Nuc. Acids Res.,* 1992, 20(3):445–447.

Henderson, E., "Imaging of Living Cells by Atomic Force Microscopy" *Progress in Surface Science,* May 1994, 46(1):39–60.

Henderson, E., "Molecular force detection and spectroscopy with the atomic force microscope" *Science Progress,* 1998, 81(2):141–151.

Henderson, E., et al., "Actin Filament Dynamics in Living Glial Cells Imaged by Atomic Force Microscopy" *Science,* 1992, 257:1944–1946.

Henderson, E., et al., "New Ribosome Structure" *Science,* 1984, 255:510–512.

Henderson, E., et al., "Telomeric DNA oligonucleotides form novel intramolecular structures containing guanine–guanine base pairs" *Cell,* 1987, 51(6):899–908.

Henderson, et al., "A method for gold coating experimental detector beampipes" htttb://www.Ins.cornell.edu/public/CNB/1999/CBN99–7/cbn99–7.pdf, 1999.

Hiller, et al., "Microarrayed allergen molecules: diagnostic gatekeepers for allergy treatment" *FASEB,* 2002, 16:414–416.

Hinterdorfer, P. et al., "Detection and localization of individual antibody–antigen recognition events by atomic force microscopy" *PNAS,* 1996, 93:3477–3481.

Hoh, J.H., and Hansma, P.K., "Atomic force microscopy for high resolution imaging in cell biology" *Trends in Cell Biology,* 1992, 2:208–213.

Hoh, J.H., et al., "Atomic force microscopy and dissection of gap junctions" *Science,* 1991, 1405–1408.

Hoh, J.H., et al., "Quantized adhesion detected with the atomic force microscope," *J. Am. Chem. Soc.,* 1992, 114:4917–4918.

Holland, Vacuum Deposition Of Thin Films (Wiley, New York, NY, 1956) (Book Reference Not Being Provided).

Hong, et al., "A new tool for studying the in situ growth processes for self–assembled monolayers under ambient conditions" *Langmuir,* 1999, 15:7879–7900.

Hong, et al., "Multiple ink nanolithography: toward a multiple–pen nano–plotter" *Science,* 1999, 286:523–525.

Hong, S. et al. "A Nanoplotter with Both Parallel and Serial Writing Capabilities" *Science,* Jun. 9, 2000, 288:1808–1811.

Hovis, et al., "Cyloaddition chemistry and formation of ordered organic monolayers on silicone (001) surfaces" *Surface Science,* 1998, 402–404, pp. 1–7.

Hovis, et al., "Structure and bonding of ordered organic monolayers of 1,5–cyclooctadiene on the silicon (001) Surface" *J. Phys. Chem. B.,* 1997, 101:9581–9585.

Hu, et al., "Imaging the condensation and evaporation of molecularly thin films of water with nanometer resolution" *Science,* 1995, 268(5208):267–269.

Huck, et al., "Patterned polymer multilayers as etch resists" *Langmuir,* 1999, 15:6862–6867.

Ivanisevic, et al., "Dip–Pen Nanolithography on Semiconductor Surfaces" *J. Am. Chem. Soc.,* 2001, 123:7887–7889.

Iyer, et al., "The Transcription Program in the Response of Human Fibroblasts to Serum" *Science,* 1999, 283(5398):83–87.

Jackman, et al., "Fabrication of submicrometer features on curved substrates by microcontact printing" *Science,* 1995, 269: 664–666.

James, et al., "Patterned protein layers on solid substrates by thin stamp microcontact printing" *Langmuir,* 1998, 14:741–744.

Janes, et al., "Electronic conduction through 2D arrays of nanometer diameter metal clusters" *Superlattices and Microstrucures,* 1995, 18(4):275–282.

Jaschke, et al., "Deposition of organic material by the tip of a scanning force microscope" *Langmuir,* 1995, 11:1061–1064.

Jin, X., Unertl, W., "Submicrometer modification of polymer surfaces with a surface force microscope" *Applied Physics Letters,* 1992, 61(6):657–659.

Jones, V., et al., "Microminiaturized Immunoassays Using Atomic Force Microscopy and Compositionally Patterned Antigen Arrays 66" Anal. Chem., 1998, 70(7):1233–1241.

Karpovich, et al., "Direct measurement of the adsorption kinetics of alkanethioilate self–assembled monolayers on microcrystalline gold surface" *Langmuir,* 1994, 10:3315–3322.

Kim, et al., "Nanotube nanotweezers" *Science,* Dec. 10, 1999, 286:2148–2150.

Knezevic et al., "Proteomic profiling of the cancer microenvironment by antibody arrays" *Proteomics,* 2001,. 1:1271–1278.

Kochanek, et al., "Transcriptional silencing of human ALU sequences and inhibition of protein binding in the box B regulatory elements by 5'CG3 " methylation" *FEBS Lett.,* 1995, 360(2):115–120 [PMID 7875314] Abstract.

Komeda, et al., "Octadecyltrichlorosilane self– assembled–monolayer islands as a self–patterned–mask for HF etching of $SiO_2$ on Si" *J. Vac. Sci. Technol A.,* 1998, 16(3):1680–1685.

Kumar, et al., "The use of self–assembled monolayers and a selective etch to generate patterned gold features" *J. Am. Chem. Soc.,* 1992, 114:9188–9189.

Lahiri, et al., "Patterning ligands on reactive SAMs by microcontact printing" *Langmuir,* 1999, 15, 2005–2060.

Laibinis et al., "ω–terminated alkanethiolate monolayers on surfaces of copper, silver, and gold have similar wettabilities" *J. Am. Chem. Soc.,* 1992, 114: 1990–1995.

Lal, R. and John, S.A., "Biological applications of atomic force microscopy" *Am. J. Physiology,* 1994, 266(1):1–21.

Lanio, T., et al., "PCR–based random mutagenesis method using spiked oligonucleotides to randomize selected parts of gene without any wild–type background" *Biotechniques,* 1998, 25(6):958–965.

Lee, et al., "Nanometer–scale lithography on H–passivated Si(100) by atomic force microscope in air" *J. Vac. Sci. Tecnnol. A.,* 1997, 15(3):1451–1454.

Lee, G. et al., "Direct measurement of the forces between complementary strands of DNA" *Science,* 1994, 266:771–773.

Lercel, et al. "Self–assembled monolayer electron–beam resists on GaAs and $SiO_2$" *J. Vac. Sci. Technol. B.,* 1993, 11(6): 2823–2828.

Lercel, et al., "Sub–10nm lithography with self–assembled monolayers" *Appl. Phys. Lett.,* 1996, 68(11):1504–1506.

Liu, et al., "Nanofabrication of self–assembled monolayers using scanning probe lithography" *Acc. Chem. Res.,* 2000, 33(7):457–466.

Lo, et al., "Organic and inorganic contamination on commercial AFM cantilevers" *Langmuir,* 1999, 15:6522–6526.

Luthi, et al., Parallel nanodevice fabrication using a combination of shadow mask and scanning probe methods: *Aplied Physics Letters,* 1999, 75(9):1314–1316.

Lutwyche, et al., "5X5 2D AFM cantilever arrays a first step toward Terabit storage device" *Sensors and Actuators,* 1999, 73:89–94.

Lynch, M., et al., "A Reliable Preparation Method for Imaging DNA by AFM" *Microscopy Today,* 1999, 99(9) 1 pg.

Lyubchenko, Y.L., et al., "Atomic force microscopy of DNA and bacteriophage in air, water and propanol: The role of adhesion forces" *Nuc. Acids Res.,* 1993, 21(5):1117–1123.

Macaya, et al., "Thrombin–binding DNA aptamer forms a unimolecular quadruplex structure in solution" *PNAS USA,* Apr. 1993, 90:3745–3749.

MacBeath, G. and Schreiber, S.L., "Printing Proteins as Microarrays for High–Throughput Function Determination" *Science,* Sep. 8, 2000, 289:1760–1763.

Magno, R., Bennett, B., "Nanostructure patterns written in III–V semiconductors by an atomic force microscope" *Applied Physics Letters,* 1997, 70(14):1855–1857.

Malmborg, et al., "Real Time Analysis of Antibody–Antigen Reaction Kinetics", *Scand. J. Immunol.,* 1992, 35:634–650.

Marsh, T.C., et al., "A new DNA nanostructure imaged by scanning probe microscopy" *Nuc. Acids Res.* 1995, 23(4):696–700.

Marsh, T.C., et al., "G–wires: Self–assembly of a telometic oligonucleotide, d(GGGGTTGGGG), into large superstructures" *Biochemistry* 1994, 33:10718–10724.

Martin, B., et al., "Ortogonal Self–Assembly on Colloidal Gold–Platinum Nanorods" *Advanced Materials,* 1999, 11:1021.

Matteucci, et al., "Synthesis of deoxyoligonucleotides on a polymer support I" *J. Am. Chem. Soc.,* 1981, 103:3185–3191.

Maynor, et al., "Au:Ink" for AFM "Dip–Pen" Nanolithography *Langmuir,* 2001, 17:2575–2579.

Mazzola, L., "Discrimination of DNA hybridization using chemical force microscopy" *Biophysical Journal,* 1999, 76:2922–2933.

Mazzola, L., "Imaging biomolecule arrays by atomic force microscopy" *Biophysical Journal,* 1995, 68:1653–1660.

McEuen, et al., "Crossed Nanotube Junctions" *Science,* Apr. 21, 2000, 288:494–497.

Meister, et al., "Nanoscale Dispensing of Liquids through Cantilevered Probes" *MNE '02* Lugano, Switzerland, Sep. 16–19, 2002.

Mendoza, et al., "High–Throughput Microarray–Based Enzyme–Linked Immunosorbent Assay (ELISA)" *BioTechniques,* 1994, 27(4):778–788.

Meyer, G. and N.M. Amer, "Novel optical approach to aotmic force microscopy" *Appl. Phys. Lett.,* 1988, 53:1045–1047.

Minne, et al., "Centimeter scale atomic force microscope imaging and lithography" *Applied Physics Letters,* 1998, 73(12):1742–1744.

Minne, S.C., et al., "Automated parallel high–speed atomic force microscopy" *Appl. Phys. Lett.,* 1998, 72(18):2340–2342.

Mirkin, et al., "Dip–Pen Nanolithography: Controlling Surface Architecture on the Sub–100 Nanometer Length Scale" *Chemphyschem,* 2001, 2:37–39.

Mirkin, et al., "Programming the Assembly of Two– and Three–Dimensional Architectures with DNA and Nanoscale Inorganic Building Blocks Invited Contribution from Recipient of ACS Award in Pure Chemistry" *Inorg. Chem.,* 2000, 39:2258–2272.

Mosher, C., et al., "NanoArrays, The Next Generation Molecular Array Format for High Throughput Proteomics, Diagnostics and Drug Recovery" *JALA,* 2000, 5(5):75–83.

Moy, et al., "Intermolecular Forces and Energies Between Ligands and Receptors" *Science,* 1994, 266:257–259.

Moy, V.T., et al., "Probing the forces between complimentary strands of DNA with the atomic force microscope" *SPIE,* 1995, 2384:2–12.

Mueller, et al., "Atomic force microscopy deposition of poly–l–lysine structures onto lipid bilayers supported by mica" *Langmuir,* 2000, 16:9568–9570.

Müller, et al., "Nanostructuring of alkanethiols with ultrastrap filed emitters" *J. Vac. Sci. Technol. B.,* 1995, 13(6):2846–2849.

Murray, et al., "Atomic force microscopy of biochemically tagged DNA" *Proc., Natl., Acad. Sci.,* 1993, 90:3811–3814.

Musil, C., Nanostructuring of gold electrodes for immunosensing applications: *J. Vac. Sci. Technol. B.,* 1995, 13(6):2781–2786.

Niu, et al., "Atomic force microscopy of DNA–colloidal gold and DNA–protein complexes" *SPIE Advances in DNA Sequencing Technology,* 1993, 1891:71–77.

Noy, et al., "Chemical force microscopy: exploiting chemically–modified tips to quantify adhesion, friction, and functional group distributions in molecular assemblies" *J. Am. Chem.,* 1995, 117:7943–7951.

Noy, et al., "Chemically–sensitive imaging in tapping mode by chemical force microscopy: relationship between phase lag adhesion" *Langmuir,* 1998, 14:1508–1511.

Nuzzo, R., "Spontaneously organized molecular assemblies. 3. Preparation and properties of solution adsorbed monolayers of organic disulfides on gold surfaces" *J. Am. Chem. Soc.*, 1987, 109:2358–2368.

Nyffenegger, et al., "Nonometer scale surface modification using the scanning probe microscope: progress since 1991" *Chem. Rev.*, 1997, 97:1195–1230.

O'Brien, J., et al., "Immunosensing Platforms Using Spontaneously Absorbed Antibody Fragments on Gold" *Analytical Chemistry*, 2000, 72(4):703–710 [PMID 10701253] Abstract.

Oshio, T. et al., "Atomic force microscopy detection system using an optical fiber heterodyne interferometer free from eternal disturbances" *Ultramicroscopy* 42–44 (Jul. 1992) 310–314.

Paweletz, et al., "Reverse phase protein microarrays which capture disease progression shoe activation of pro–survival pathways at the cancer invasion front" *Oncogen*, 2001, 20:1981–1989.

Pawlak, et al., "Zeptosens' protein microarrays: A novel high performance microarray platform for low abundance protein analysis" *Proteomics*, 2002,. 2:383–393.

Perkins, et al., "Fabrication of 15 nm wide trenches in Si by vacuum scanning tunneling microscope lithography of an organosilane self–assembled film and reactive ion etching" *Appl. Phys. Lett.*, 1996, 68(4):550–552.

Pfannschmidt, et al., "Sequence–specific labeling of superhelical DNA by triple helix formation and psoralen crosslinking" *Nucleic Acids Research*, 1996 24(9):1702–1709.

Piner, et al., "Improved imaging of soft materials with modified AFM tips" *Langmuir*, 1999, 15:5457–5460.

Piner, R.D., et al., "Dip–Pen Nanolithography" *Science*, Jan. 29, 1999,283(5402):661–663.

Piner, Richard, "Effect of water on lateral force microscopy in air" *Langmuir*, 1997, 13:6864–6868.

Putnam, C.A.J., "Tapping atomic force microscopy in liquids" *Appl. Phys. Lett.*, 1994, 64(18):2454–2456.

Qin, et al., Fabrication of ordered two–dimensional arrays of micro– and nanoparticles using patterned self–assembled monolayers as templates: *Adv. Matter*, 1999, 11(17):1433–1437.

Rankin, P.C. Wilson, A.T. "The Surface Chemsitry of the Mica–Aluminum–Sulfate System" *Journal of Collid and Interface Science*, (1969) 30(3):277–282.

Reed, et al., "Conductance of molecular junction" *Science*, 1997, 278:252–254.

Rief, et al., "Reversible unfolding of individual Titin Ig–domains by AFM" *Science*, 1997, 276:1109–1111.

Rief, M., et al., "Single Molecule Force Spectroscopy on Polysaccharides by Atomic Force Microscopy" *Science*, 1997, 275:1295–1297.

Rief, M., et al., "The mechanical stability of immunoglobulin and fibronectin III domains in the muscle protein titin measured by atomic force microscopy" *Biophyiscal Journal*, 1998, 3008–3014.

Robinson, et al., Autoantigen microarrays for multiplex characterization of autoantibody responses *Nature Medicine*, Mar. 2002, 8(3):1–7.

Santos, et al., "Probing hydrophobic interactions of surfaces and macromolecules with atomic force microscope" *Book of Abstracts*, 214 ACS National meeting, Sep. 7–11, 1997, PHYS–248.

Sastry, et al., "Formation of patterned hetrocolloidal nanoparticle thin films" *Langmuir*, 2000, 16:3553–3556.

Schaus, S., et al., "Cell Viability and Probe–Cell Membrane Interactions of XR1 Glial Cells Imaged by Atomic Force Microscopy" *Biophysical Journal*, Sep. 1997, 73:1205–1214.

Schena, et al., "Parallel human genome analysis: Microarray–based expression monitoring of 1000 genes" *PNAS USA*, 1996, 93:10614–10619.

Schena, M., *Microarray Biochip Technology*, Eaton Publishing, NatickMA 2000. (Book Reference Not Being Provided).

Schoer, et al., "Scanning probe lithography. 4. Characterization of scanning tunneling microscope–induced patterns in *n*–Alknethiol self–assembled monolayers" *Langmuir*, 1997, 13:2323–2332.

Schumacher, et al., "Nanomachining of mesoscopic electronic devices using an atomic force microscope" *Applied Physics*, 1999, 75(8):1107–1109.

Schwartz, et al. "Meniscus Force Nanografting: Nanoscopic Patterning of DNA" *Langmuir*, 2001, 17:5971–5977.

Schwartz, et al., "Molecular Transport from an Atomic Force Microscope Tip: A Comparative Study of Dip–Pen Nanolithography" *Langmuir*, American Chemical Society, Nov. 6, 2001.

Schweitzer, et al., "Multiplexed protein profiling on microarrays by rolling–circle amplification" *Nature Biotechnology*, Apr. 2002, 20:359–365.

Shaiu, W.L., et al., "Atomic Force Microscopy of Oriented Linear DNA Molecules Labeled with 5nm Gold Spheres" *Nuc. Acids Res.*, 1993, 21(1):99–103.

Shaiu, W.L., et al., "Visualization of circular DNA molecules labeled with colloidal gold spheres using atomic force microscopy" *J. Vac. Sci. Technol. A.*, 11(4):820–823.

Sheehan, et al., "Thiol diffusion and the role of humidity in "dip pen" nanolithography" *Physical Review Letters*, Apr. 15, 2002, 88(15):156104–1–156104–4.

Sheen, et al., "A new class of organized self–assembled monolayers: alkane thiols on GaAs (100)" *J. Am. Chem. Soc.*, 1992, 114:1514–1515.

Sherman, Chemical Vapor Deposition For Microelectornices: Principles. Technology and Applications (Noyes, Park Ridges, NJ, 1987). (Book Reference Not Being Provided).

Shlyakhtenko, L.S., et al., "Structure and dynamics of supercoil–stabilized DNA cruciforms" *J. Mol. Biol.*, 1998, 280(1):61–72.

Shlyakhtenko, L.S., Gall, A.A., et al., "Atomic force microscopy imaging of DNA covalently immobilized on a functionalized mica substrate" *Biophysical Journal*, Jul. 1999, 77:568–576.

Silzel, et al., "Mass–sensing, multianalyte microarray immunoassay with imaging detection" *Clinical Chemistry*, 1998, 44(9):2036–2043.

Smalley, et al., "Nanotube Device" *Science*, Oct. 3, 1997, 278:100–103.

Smith et al., "Overstretching B–DNA: the elastic response of individual double–stranded and single stranded DNA molecules" *Science*, Feb. 9, 1996, 271:795–799.

Snow, et al., "High speed patterning of a metal silicide using scanned probe lithography" *Applied Physics Letters*, 1999, 75(10):1476–1478.

Soh, H., et al., "Integrated nanotube circuits: controlled growth and ohmic contacts to single–walled–carbon nanotubes" *Appl. Phys. Letts.*, 1999, 75(5):627–629.

Sondag–Huethorst, et al., "Generation of electrochemically deposited metal patterns by means of electron beam (nano-)lithography of self–assembled monolayer resists" *Appl. Phys. Lett.* 1994, 64(3):285–287.

Southern, E.M., "Detection of specific sequences among DNA fragments separated by gel electrophoresis" *J. Mol. Biol.* 1975, 98:503–517.

Spectroscopy Europe—News Feb./Mar. 2002, 6 pages, http://www.spectroscopyeurope.com/news14_1.html.

Spence, J., Weierstall, U., et al., "Atomic species identification in scanning tunneling microscopy by time of flight spectroscopy" *J. Vac. Sci. Tech.,* 1996, B14(3):1587–1590.

Sreekumar, et al., "Profiling of cancer cells using protein microarrays: Discovery of novel radiation–regulated proteins" *Cancer Research,* 2001, 61:7585–7593.

Steiner, et al., "Adsorption of alkanenitriles and alkanedinitriles on gold and copper" *Langmuir,* 1992, 8:2271–2777.

Stökle, R., Setz, P. "Nanoscale Atmospheric Pressure Laser Ablation–Mass Spectrometry" *Anal. Chem.,* 2001, 73(7):1399–1402.

Su, et al., "Moving beyond Molecules: Patterning Solid–State Features via Dip–Pen Nanolithography with Sol–Based Inks" *JACS,* 2002, 124(8):1560–1561.

Sun, et al., "Nanoscale Molecular Patterns Fabricated by Using Scanning Near–Field Optical Lithography" *JACS,* 2002, 124(11):2414–2415.

Tang, K., Fu, D., et al., "Matrix–assisted laser desorption/ionization mass spectrometry of immobilized duplex DNA probes" *Nucleic Acids Research,* 1995, 23(16):3126–3131.

Tans, et al., "Room–temperature transistor based on a single carbon nanotube" *Nature,* May 7, 1998, 393:49–52.

Tarlow, M.J., Newman, J.G., et al., "Static secondary ion mass spectrometry of self–assembled alkanethiol monolayers on gold" *Langmuir,* 1992, 8:1398–1405.

Tien, et al., "Microfabrication through electrostatic self–assembly" *Langmuir,* 1997, 13:5349–5355.

Troughton, E., Bain, C., et al., "Monolayer films prepared by the spontaneous self–assembly of symmetrical and unsymmetrical dialkyl sulfides from solution onto gold substrates: Structure, properties and reactivity of constituent functional groups" *Langmuir,* 1988, 4:365–385.

Tsukamoto, et al. "Twin–probe scanning tunneling microscope" *Rev. Sci. Instrum.,* Jul. 1991, 62(7):767–1771.

Uetz, P., et al., "A comprehensive analysis of protein–protein interactions in *Saccharomyces cerevisiae*" *Nature,* Feb. 10, 2000, 403(6770):623–627.

Ulman, Abraham, "Formation and structure of self–assembled monolayers" *Chem. Rev.,* 1996, 96:1533–1554.

Ulman, An Introduction to Ultrathin Organic Films: From Langmuir–Blodgett to Self–Assembly (Academic, Boston 1991) (Alkanethiols on gold). (Book Reference Not Being Provided).

Vesenka, J. et al., "A substrate, preparation for reliable imaging of DNA molecules with the scanning force microscope" *Ultramicroscopy,* 1992, 42–44:1243–1249.

Vesenka, J., et al., "Colloidal gold particles as an incompressable atomic force microscope imaging standard for assessing the compressability of biomolecules" *Biophys. J.,* 1993, 65:992–997.

Vesenka, J., et al., "Combining optical and atomic force microscopy for life sciences research" *BioTechniques,* 1995, 19(2):240–253.

Vettiger, et al., "Ultrahigh density, high–data–rate NEMS–based AFM data storage system" *Microelectronic Engineering,* 1999, 46:11–17.

Vezenov, Dmitri, "Force titrations and ionization state sensitive imaging of functional groups in aqueous solutions by chemical force microscopy" *J. Am. Chem. Soc.,* 1997, 119:2006–2015.

Vossmeyer, et al., "Combinatorial approaches toward patterning nanocrystals" *Journal of Applied Physics,* 1998, 84(7):3664.

Wadu–Mesthrige, et al., "Fabrication and imaging of nanomneter–sized protein patterns," *Langmuir,* 1999, 15:8580–8583.

Wallraff, et al., "Lithographic imaging techniques for the formation of nanoscopic features" *Chem. Rev.,* 1999, 99:1801–1821.

Walters, D.A., Hampton, A.D., et al. "Atomic force microscope integrated with a scanning electron microscope for tip fabrication" *Applied Physics Letters,* Aug. 8, 1994, 65(6):787–789.

Wang, et al., "Nanometer scale patterning and pattern transfer on amorphous Si, crystalline Si, and $SiO_2$ surfaces using self–assembled monolayers" *Appl. Phys. Lett.,* 1997, 70(12):1593–1595.

Weierstall, U. Spense, J. "Atom species identification in STM using an Imaging Atom–Probe technique" *Surface Science* 1998, 398:267–279.

Whitesides, et al., "Self–assembled monolayers and lithography" *Nanophase Chemistry* 1995, 39:109–122.

Wilbur, et al., "Scanning force microscopes can image patterned self–assembled monolayers" *Langmuir,* 1995, 11:825–831.

Williamson, et al., "G–quartets in biology: Reprise" *PNAS USA,* Apr. 15, 1993, 90(8):3124–3124.

Williamson, et al., "Monovalent cation–induced structured of telomeric DNA: The G–quartet model" *Cell,* 1989, 59(5):871–880.

Wilson, et al., "Surface organization and nanopatterning of collagen by dip–pen nanolithography" *PNAS,* Nov. 20, 2001, 98(24):13660–13664.

Wong, S., et al., "Covalently functionalized nanotubes as nanometre–sized probes in chemistry and biologu" *Nature,* 1998, 394:52–55.

Wong, S., et al., "Covalently functionalized single–walled carbon nanotube probe tips for chemical force microscopy" *Journal of the American Chemical Society,* 1998, 120:8557–8558.

Wong, S., et al., "Functionalization of carbon nanotube AFM probes using tip–activated gases" *Chem Physics Letters,* 1999, 306:219–225.

Xia, et al., "A selective etching solution for use with patterned self–assembled monolayers of alkanethiolates on gold" *Chem. Mater.,* 1995, 7:2332–2337.

Xia, et al., "Complex optical surfaces formed by replica molding against elastomeric masters" *Science,* 1996, 273:347–349.

Xia, et al., "Pattern transfer: self–assembled monolayers as ultrathin resists" *Microelectronic Engineering,* 1996, 32:255–268.

Xia, et al., "Soft lithography" *Agnew Chem. Int. Ed.,* 1998, 37:551–575.

Xia, et al., "Unconventional methods for fabricating and patterning nanostructures" *Chem. Rev.,* 1999, 99:1823–1848.

Xu, et al., "Fabrication of nanometer scale patterns within self–assembled monolayers by nanografting" *Langmuir,* 1999, 15:7244–7251.

Xu, et al., Nanometer–scale fabrication by simultaneous nanoshaving and molecule self–assembly: *Langmuir,* 1997, 13:127–129.

Xu, et al., "Wetting and capillary phenomena of water on mica" *J. Phys. Chem. B.,* 1998, 102:540–548.

Yan Li, et al., "Electrochemical AFM "Dip–Pen" Nanolithography" *J. Am. Chem., Soc.* 2001, 123:2105–2106.

Yan, et al. "Patterning a performed, reactive SAM using microcontact printing" *J. Am. Chem. Soc.,* 1998, 120:6179–6180.

Yan, et al., "Patterning thin films of poly(ethylene imine) on a reactive SAM using microcontact printing" *Langmuir,* 1999, 15:1208–1214.

Ying, et al., "Programmable Delivery of DNA through a Nanopipet" *Anal. Chem.,* 2002, 74:1380–1385.

Youil, R., Screening for mutations by enzyme mismatch cleavage with T4 endonuclease VII*PNAS USA,* 1995, 92(1):87–91.

Zhong, Q., et al., "Fractured polymer/silica fiber surface studies by tapping mode atomic force microscopy" *Surf. Sci. Lett.,* Jan. 3, 1993, 290: L 688–L692.

Zhu, et al., "Analysis of yeast protein kinase using protein chips" *Nauture Genetics,* 2000, 26:283–289.

Zhu, et al., "Global Analysis of Protein Activities Using Proteome Chips" *Science,* Sep. 2001, 293(14):2101–2105.

Binning et al., *Surface studies by scanning tunneling microscopy,* Phys. Rev. Lett., 1982, 49: p. 57–61.

Cheng et al, *Electric field controlled preparation and hybridization analysis of DNA/RNA from E coli on microfabricated bioelectronic chips,* Nature Biotechnology, 1998, 16: p. 541–546.

Dammer et al., *Binding strength between cell adhesion proteoglycans measured by atomic force microscopy,* Science, 1995, 267: p. 1173–1175.

Dammer et al., *Specific antigen/antibody interactions measured by force microscopy,* Biophys. J., 1996, 70: p. 2437–2441.

Florin et al., *Adhesion forces between individual ligan–receptor pairs, Science,* 1994, 264: p. 415–417.

Fodor et al., *Light–directed spatially addressable parallel chemical synthesis,* Science, 1991, 251: p. 767–773.

Fodor et al., *Multiplexed biochemical assays with biological chips,* Nature, 1993, 364: p. 555–557.

Hinterdorfer et al.; *Detection and localization of individual antibody–antigen recognition events by atomic force microscopy,* Proc. Natl. Acad. Sci., 1996, 93: p. 3477–3481.

Jones et al., Microminiaturized immunoassays using atomic force imcroscopy and compositionally patterned antigen arrays, Analy. Chem., 1998, 70(7): p. 1233–1241.

Lee et al., *Direct measurement of the forces between complementary strands of DNA,* Science, 1994, 266: p. 771–773.

Iyer et al., *The Transcription Program in the Response of Human Fibroblasts to Serum,* Science, 1999, 283(5398): p. 83–87.

Moy et al., *Intermolecular Forces and Energies Between Ligands and Receptors,* Science, 1994, 266: p. 415–417.

Rief et al., *Single Molecule Force Spectroscopy on Polysaccharides by Atomic Force Microscopy,* Science, 1997, 275: p. 1295–1297.

Rief et al, *Reversible Unfolding of Individual Titin Ig–domains by AFM,* Science, 1997, 276: p. 1109–1111.

Dontha, Narasaiah, et al. "Generation of Biotin/Avidin/ Enzyme Nanostructues with Maskless Photoligography", Anal. Chem , vol. 69, (1997), pp. 2619–2625.

Fritzsche, Wolfgang, et al. "Chicken Erythrocyte Nucleosomes Have a Defined Orientation along the Linker DNA–A Scanning Force Microscopy Study", Scanning, vol. 19, (1997), pp. 42–47.

Fritzsche, Wolfgang, et al. "Mapping elasticity of rehydration metaphase chromosomes by scanning force microscopy", Ultramicroscopy, vol. 69, (Feb. 1997), pp. 191–200.

Fritzsche, Wolfgang, et al. "Ribosome substructure investigation by scanning force microscopy and image processing", Journal of Microscopy, vol. 189,Pt 1, (Jan. 1998), (pp. 50–56).

Fritzsche, Wolfgang, et al. "Application of Atomic Force Microscopy to Visualization of DNA, Chromatin and Chromosomes", Critical Reviews™ in Eukarytotic Gene Expression vol. 7, No. 3, (1997), pp. 231–240.

Henderson, Eric "Molecular force detection and spectroscopy with the atomic force microscope", Science Progress, vol. 81, No. 2 (1998), pp. 141–151.

Henderson, Eric "Atomic force microscopy of conventional and unconventional nucleic acid structures", Journal of Microscopy, vol. 167, (Jul. 1992), pp. 77–84.

Henderson, Eric, et al. "Actin Filament Dynamics in Living Glial Cells Imaged by Atomic Force Microscopy", Science, vol. 257, (Sep. 25, 1992), pp. 1944–1946.

Jones, Vivian et al. "Microminiaturized Immunoassays Using Atomic Force Microscopy and Compositionally Patterned Antigen Arrays", Anal. Chem. , vol. 70 (1998), pp. 1233–1241.

Lynch, Michael et al., "A Reliable Preparation Method for Imaging DNA by AFM", Microscopy Today, vol. 99, No. 9, (1999); 1 pg.

Mazzola, Laura, T. et al., "Discrimination of DNA Hybridization Using Chemical Force Microscopy", *Biophysical Journal,* vol. 75, (Jun. 1999), pp. 2922–2933.

Mosher, Curtis, et al., "NanoArrays, The Next Generation Molecular Array Format for High Throughput Proteomics, Diagnostics and Drug Recovery", JALA, vol. 5, No. 5, (Nov. 2000); pp. 75–83.

O'Brien, Janese C., et al. "Immunosensing Platforms Using Spontaneously Absorbed Antibody Fragments on Gold", Analytical Chemistry, vol. 72, No. 4, (Feb. 15, 2000): pp. 703–710.

Schaus, Scott S., et al., "Cell Viability and Probe–Cell Membrane Interactions of XR1 Glial Cells Imaged by Atomic Force Microscopy", Biophysical Journal, vol. 73, (Sep. 1997), pp. 1205–1214.

Abstracts of Papers Part I, 214$^{th}$ "Abstract 027" *ACS National Meeting American Chemical Society,* (Sep. 1997) 2 pgs.

Alves, Carla A. et al., "Atomic Scale Imaging of Alkanethiolate Monolayers at Gold Surfaces with Atomic Force Microscopy", *J. Am. Chem. Soc.,* vol. 114, No. 4, (Feb. 12, 1992), 4 pgs.

Amro, Nabil, A., et al., "Patterning Surfaces Using Tip–Directed Displacement and Self–Assembly", *Langmuir,* (2000), 16, pp. 3006–3009.

Anwander, Reiner, et al., "Surface Characterization and Functionalization of MCM–41 Silicas via Silazane Silylation", *J. Phys. Chem. B.* (2000), 104, pp. 3532–3544.

Bain, Colin D. et al., "Modeling Organic Surfaces with Self–Assembled Monolayers", *Agnew. Chem. Int. Ed. Engl.* 28 (1989), No. 4, 5 pgs.

Berggren, Karl K. et al., Microlithography by Using Neutral Metastable Atoms and Self–Assembled Monolayers, *Science,* vol. 269, (Sep. 1, 1995), pp. 1255–1257.

Bernard, Andre et al. "Printing Patterns of Proteins", *Langmuir The ACS Journal of Surfaces and Colliods,* vol. 14, No. 9, (Apr. 28, 1998), 5 pgs.

Binggeli, M. et al., "Influence of Capillary Condensation of Water on Nanotribology Studies by Force Microscopy" *Appl. Phys. Lett.* 65(4), (Jul. 25, 1994), pp. 415–417.

Bishop, Adeana R., et al., "Self–assembled monolayers: recent developments and applications", Colloid & Interface *Science, vol. 1, No. 1,* (Feb. 1996); 6pgs.

Brandow, Susan L., Metal Pattern Fabrication Using the local electric field of conducting atomic force microscope probe, *J. Vac. Sci. Technol.,* A 15(3), (May/Jun. 1997), pp. 1455–1459.

Bottomley, Lawrence A., "Scanning Probe Microscopy", *Anal. Chem., vol. 70, No. 12,* (Jun. 15, 1998); pp. 425R–475R.

Carr, D. W., et al., High–selectivity pattern transfer process for self–assembled monolayer electron beam resists, *J. Vac. Sci. Technol. A.,* 15(3), (May/Jun. 1997), pp. 1446–1450.

Dubois, Lawrence H., et al., "Synthesis, Structure, and Properties of Model Organic Surfaces" *Annu. Rev. Phys. Chem.,* 1992, 43:437–463.

Fujihira, Masamichi et al., "Effect of Capillary Force on Friction Force Microscopy: A Scanning Hydrophilicity Microscope", *Chemistry Letters, No. 7* (Jul. 1996), 2pgs.

Grabar, Katherine C. et al., "Preparation and Characterization of Au Colloid Monolayers", *Anal. Chem., vol. 67, No. 4,* (Feb. 15, 1995), pp. 735–743.

Hong, Seunghun, et al., "A New Tool for Studying the in Situ Growth Processes for Self–Assembled Monolayers under Ambient Conditions", *Langmuir, vol. 15,* (1999), pp. 7879–7900.

Hong, Seunghun, et al., "Multiple Ink Nanolithography: Toward a Multiple–Pen Nano–Plotter", *Science, vol. 286,* (Oct. 1999), pp. 523–525.

Hovis, J.S., et al., Cyloaddition chemistry and formation of ordered organic monolayers on silicone (001) Surfaces, *Surface Science 402–404* (1998), pp. 1–7.

Hovis, Jennifer S., et al., Structure and Bonding of Ordered Organic Monolayers of 1,5–Cyclooctadiene on the Silicon(001) Surface *J. Phys. Chem. B., vol. 101,* (1997), pp. 9581–9585.

Hu, et al., "Imaging the Condensation and Evaporation of Molecularly Thin Films of Water with Nanometer Resolution", *Science, vol. 268, No. 5208,* (Apr. 14, 1995), pp. 267–269.

James, C.D., et al., "Patterned Protein Layers on Solid Substates by Thin Stamp Microcontact Printing", *Langmuir vol. 14,* (1998), pp. 741–744.

Janes, D.B., et al., "Electronic conduction through 2D arrays of nanometer diameter metal clusters" *Superlattices and Microstructures, vol. 18, No. 4* (1995), pp. 275–282.

Jaschke, Manfred, et al., "Deposition of Organic Material by the Tip of a Scanning Force Microscope" *Langmuir,* vol. 11, (Nov. 14, 1994), pp. 1061–1064.

Karpovich, D.S. et al, "Direct Measurement of the Adsorption Kinetics of Alkanethioilate Self–Assembled Monolayers on Microcrystalline Gold Surface", *Langmuir,* vol. 10, (Jun. 15, 1994), pp. 3315–3322.

Komeda, T., et al., "Octadecyltrichlorosilane self–assembled–monolayer islands as a self–patterned–mask for HF etching of $SiO_2$ on Si", *J. Vac. Sci. Technol A., 16(3),* (May/Jun. 1998), pp. 1680–1685.

Huck, Wilhelm, T.S., et al., "Patterned Polymer Multilayers as Etch Resists", Langmuir, vol. 15, (1999), pp. 6862–6867.

Lahiri, Joydeep et al., "Patterning Ligands on Reactive SAMs by Microcontact Printing", *Langmuir, vol. 15,* (1999), pp. 2055–2060.

Laibinis, Paul E., et al., ω–Terminated Alkanethiolate Monolayers on Surfaces of Copper, Silver, and Gold Have Similar Wettabilities[1], *J. Am. Chem. Soc., vol. 114, (Apr. 18, 1991),* pp. 1990–1995.

Lee, Hal Tal, et al., "Nanometer–scale lithography on H–passivated Si(100) by atomic force microscope in air", *J. Vac. Sci. Technol. A. 15(3),* (May/Jun. 1997), pp. 1451–1454.

Lercel, M. J. et al. "Self–assembled monolayer electron–beam resists on GaAs and $SiO_2$", *J. Vac. Sci. Technol. B., 11(6),* (Nov./Dec. 1993), pp. 2823–2828.

Liu, Gang–Yu, et al., "Nanofabrication of Self–Assembled Monoplayers Using Scanning Probe Lithography", *Acc. Chem. Res., vol. 33, No. 7,* (2000), pp. 457–466.

Lo, Yu–Shiu, et al., "Organic and Inorganic Contamination on Commercial AFM Cantilevers", *Langmuir, vol. 15,* (1999), pp. 6522–6526.

Lutwyche, M., et al., "5X5 2D AFM cantilever arrays a first step toward Terabit storage device", *Sensors and Actuators, vol. 73,* (1999), pp. 89–94.

Matteucci, M.D., et al., "Synthesis of Deoxyoligonucleotides on a Polymer Support 1", *J. Am. Chem. Soc. vol. 103,* (1981), pp. 3185–3191.

Luthi, Roll et al., "Parallel nanodevice fabrication using a combination of shadow mask and scanning probe methods", *Physics Letters, vol. 75, No. 9,* (Aug. 30, 1999), pp. 1314–1316.

Minne, S. C., et al. "Centimeter scale atomic force microscope imaging and lithography", *Applied Physics Letters, vol. 73, No. 12,* (Sep. 21, 1998), pp. 1742–1744.

Mueller, Henning, et al., Atomic Force Microscopy Deposition of Poly–L–lysine Structures onto Lipid Bilayers Supported by Mica *Langmuir, vol. 16,* (2000); pp. 9568–9570.

Musil, Christian R., "Nanostructuring of gold electrodes for immunosensing applications", J. Vac. Sci. Technol. B 13(6), (Nov./Dec. 1995), pp. 2781–2786.

Noy, Aleksandr, et al., "Chemical Force Microscopy: Exploiting Chemically–Modified Tips to Quantify Adhesion, Friction, and Functional Group Distributions in Molecular Assemblies", *J. Am. Chem. Soc., vol. 117,* (1995), pp. 7943–7951.

Noy, Aleksandr, et al., Chemically–Sensitive Imaging in Tapping Mode by Chemical Force Microscopy: Relationship Between Phase Lag Adhesion *Langmuir, vol. 14,* (1998), pp. 1508–1511.

Nyffenegger, R.M., et al., "Nonometer–Scale Surface Modification Using the Scanning Probe Microscope: Progress since 1991", *Chem. Rev., vol. 97,* (1997), pp. 1195–1230.

Perkins, F. Keith, et al., "Fabrication of 15nm wide trenches in Sl by vacuum scanning tunneling microscope lithography of an organosilane self-assembled film and reactive ion etching", *Appl. Phys. Lett, vol. 68(4)*, (Jan. 22, 1996), pp. 550–552.

Piner, Richard D., et al., Improved Imaging of Soft Materials with Modified AFM Tips', *Langmuir, vol. 15*, (1999), pp. 5457–5460.

Piner, Richard D., et al., "Effect of Water on Lateral Force Microscopy in Air", *Langmuir, vol. 13*, (1997), pp. 6864–6868.

Piner, Richard D., et al., "Dip–Pen Nanolithography", *Science, vol. 283*, (Jan. 29, 1999), pp. 661–663.

Qin, Dong, et al., "Fabrication of Ordered Two–Dimensional Arrays of Micro– and Nanoparticles Using Patterned Self–Assembled Monolayers as Templates", *Adv. Matter, Vo. 11, No. 17*, pp. 1433–1437.

Reed, M.A., et al., "Conductance of a Molecular Junction", *Science, vol. 278, (Oct. 10, 1997)*, pp. 252–254.

Sastry, Murali et al., "Formation of Patterned Hetrocolloidal Nanoparticle Thin Films", *Langmuir, vol. 16, (2000)*, pp. 3553–3556.

Schoer, Jonathan, K., et al., "Scanning Probe Lithography. 4. Characterization of Scanning Tunneling Microscope–Induced Patterns in *n*–Alknethiol Self–Assembled Monolayers", *Langmuir, vol. 13*, (1997), pp. 2323–2332.

Schumacher, H.W., et al., Nanomachining of mesoscopic electronic devices using an atomic force microscope, *Applied Physics, vol. 75, No. 8*, Aug. 23, 1999), pp. 1107–1109.

Sheehan, P.E., et al., "Thiol Diffusion and the Role of Humidity in Dip Pen Nanolithography", *Physical Review Letters, vol. 88, No. 15*, (Apr. 15, 2002), pp. 156104-1–156104-4.

Sheen, C. Wade, et al., "A New Class of Organized Self–Assembled Monolayers: Alkane Thiols on GaAs (100)", *J. Am. Chem. Soc., vol. 14*, (1992), pp. 1514–1515.

Sondag–Huethorst, J.A.M. et al., "Generation of electrochemically deposited metal patterns by means of electron beam (nano)lithography of self–assembled monolayer resists", *Appl. Phys. Lett. 64(3)*, (Jan. 17, 1994), pp. 285–287.

Snow, E.S., et al., "High Speed patterning of a metal silicide using scanned probe lithography", *Applied Physics Letters, vol. 75, No. 10*, (Sep. 6, 1999), pp. 1476–1478.

Steiner, Ulrich, B., et al., "Adsorption of Alkanenitriles and alkanedinitriles on Gold and Copper", *Langmuir, vol. 8* (1992), pp. 2271–2777.

Tien, Joe, et al., "Microfabrication through Electrostatic Self–Assembly", *Langmuir, vol. 13*, (1997), pp. 5349–5355.

Tsukamoto, Shigemi, et al., "Twin–probe scanning tunneling microscope", *Rev. Sci. Instrum. 62(7)*, (Jul. 1991); pp. 1767–1771.

Ulman, Abraham, "Formation and Structure of Self–Assembled Monolayers", *Chem. Rev. 96*, (1996), pp. 1533–1554.

Vettiger, P., et al., "Ultrahigh density, high–data–rate NEMS–based AFM data storage system", *Microelectronic Engineering 46* (1999), pp. 11–17.

Vezenov, Dmitri, V., "Force Titrations and Ionization State Sensitive Imaging of Functional Groups in Aqueous Solutions by Chemical Force Microscopy", *J. Am. Chem. Soc., vol. 119*, (1997), pp. 2006–2015.

Vossmeyer, T., et al., Combinatorial approaches toward patterning nanocrystals, *Journal of Applied Physics, vol 84, No. 7*, (Oct. 1, 1998), pp. 3664.

Wadu–Mesthridge, Kaplia, et al., "Fabrication and Imaging of Nanometer–Sized Protein Patterns", *Langmuir, vol. 15*, (1999), pp. 8580–8583.

Wallraff, G.M., et al., "Lithographic Imaging Techniques for the Formation of Nanoscopic Features", *Chem. Rev., vol. 99*, (1999), pp. 1801–1821.

Wang, Dawen, et al., "Nanometer scale patterning and pattern transfer on amorphous Si, crystalline Si, and SiO2 surfaces using self–assembled monolayers", *Appl. Phys. Lett. vol. 70*, (Mar. 24, 1997), pp. 1593–1595.

Whitesides, George, M., et al., "Self–Assembled Monolayers and Lithography", *Nanophase Chemistry, vol. 39*, (1995), pp. 109–122.

Nuzzo, Ralph, G., "Spontaneously Organized Molecular Assemblies. 3. Preparation and Properties of Solution Adsorbed Monolayers of Organic Disulfides on Gold Surfaces", *J. Am. Chem. Soc., vol. 109*, (1987), pp. 2358–2368.

Wilbur, James L., et al., "Scanning Force Microscopies Can Image Patterned Self–Assembled Monolayers", *Langmuir, vol. 11*, (1995), pp. 825–831.

Xia, Younan, et al., "Pattern transfer: Self–assembled monolayers as ultrathin resists", *Microelectronic Engineering, vol. 32, (1996)*, pp. 255–268.

Xia, Younan, et al., "Soft Lithography", *Angew. Chem. Int. Ed., vol. 37, (1998)*; pp. 550–575.

Xia, Younan, et al., "Complex Optical Surfaces Formed by Replica Molding Against Elastomeric Masters", *Science, vol. 237, (Jul. 19, 1996)*, pp. 347–349.

Xia, Younan, et al., "Unconventional Methods for Fabricating and Patterning Nanostructures", *Chem. Rev., vol. 99, (1999)*, pp. 1823–1848.

Xia, Younan, et al., "A Selective Etching Solution for Use with Patterned Self–Assembled Monolayers of Alkanethiolates on Gold", *Chem. Mater., vol. 7, (1995)*, pp. 2332–2337.

Xu, Lei, et al., "Wetting and Capillary Phenomena of Water on Mica", *J. Phys. Chem. B., vol. 102*, pp. 540–548.

Xu, Song, et al., "Fabrication of Nanometer Scale Patterns within Self–Assembled Monolayers by Nanografting", *Langmuir, vol. 15, (1999)*, pp. 7244–7251.

Xu, Song, et al., "Nanometer–Scale Fabrication by Simultaneous Nanoshaving and Molecular Self–Assembly", *Langmuir, vol. 13, (1997)*, pp. 127–129.

Yan, Lin, et al., Patterning a Performed, Reactive SAM Using Microcontact Printing, *J. Am. Chem Soc., vol. 120*, (1998), pp. 6179–6180.

Yan, Lin, et al., Patterning Thin Films of Poly(ethylene Imine) on a Reactive SAM Using Microcontact Printing, *Langmuir, vol. 15, (1999)*, pp. 1208–1214.

Colvin, V. L. et al. "Semiconductor Nanocrystals Covalently Bound to Metal Surfaces with Self–Assembled Monolayers," *J. Am. Chem. Soc.,* (1992), 114, pp. 5521–5320.

Jackman, R. et al., "Fabrication of Semiconductor Features on Curved Substrates by Microcontact Printing", Science, vol. 269, (Aug. 4, 1995), pp. 664–666.

Lercel, M.J. et al. "Sub–10 Lithography with Self–assembled monolayers", *Appl. Phys. Lett. 66 (11)*, Mar. 11, 1996, pp. 1504–1506.

Kumar, Amit et al., "The Uses of Self–Assembled Monolayers and a Selective Etch to Generate Patterned Gold Features", *J. Am. Chem. Soc., vol. 114,* (1992), pp. 9188–9189.

Muller, H.U., et al., "Naostructuring of alkanethiols with ultrastrap field emitters", *J. Vac. Sci. Technol. B, 13(6)*, Nov./Dec. (1995), pp. 2846–2849.

Frisbe, C. Daniel et al., "Functional Group Imaging by Chemical Force Microscopy", *Science, vol. 265,* Sep. 30, 1994, pp. 2071–2074.

METHOD AND APPARATUS FOR SOLID STATE MOLECULAR ANALYSIS

RELATED APPLICATIONS

This application is a divisional of U.S. patent application Ser. No. 09/574,519, filed on May 18, 2000 now U.S. Pat. No. 6,573,369, which claims priority to U.S. Provisional Application Ser. No. 60/135,290, filed on May 21, 1999. Application Ser. No. 09/574,519 and Application Ser. No. 60/135,290 are hereby incorporated by reference in their entirety.

TECHNICAL FIELD

This invention relates to an apparatus and method for the construction and utilization of molecular deposition domains. More specifically, this invention is a method for the construction and utilization of molecular deposition domains into a high density molecular array for identifying and characterizing molecular interaction events.

BACKGROUND

Interactions between molecules is a central theme in living systems. These interactions are key to myriad biochemical and signal transduction pathways. Messages from outside a cell travel along signal transduction pathways into the cell's nucleus, where they trigger key cellular functions. Such pathways in turn dictate the status of the overall system. Slight changes or abnormalities in the interactions between biomolecules can effect the biochemical and signal transduction pathways, resulting in inappropriate development, cancer, a variety of disease states, and even cell senescence and death. On the other hand, it can be extremely beneficial to develop reagents and effectors that can inhibit, stimulate, or otherwise effect specific types of molecular interactions in biochemical systems; including biochemical and signal transduction pathways. Reagents and effectors that effect nucleus interactions may often become very powerful drugs which can be used to treat a variety of conditions.

Current Technology

Several recent studies have shown that a scanning probe microscope "SPM" may be used to study molecular interactions by making a number of measurements. The SPM measurements may include changes in height, friction, phase, frequency, amplitude, and elasticity. The SPM probe can even perform direct measurements of the forces present between molecules situated on the SPM probe and molecules immobilized on a surface. For example, see Lee, G. U., L. A. Chrisey, and R. J. Colton, *Direct Measurement of the Forces Between Complementary Strands of DNA*. Science, 1994. 266: p. 771–773; Hinterdorfer, P., W. Baumgartner, H. J. Gruber, and H. Schindler, *Detection and Localization of Individual Antibody-antigen Recognition Events by Atomic Force Microscopy*, Proc. Natl. Acad. Sci., 1996. 93: p. 3477–3481; Dammer, U., O. Popescu, P. Wagner, D. Anselmetti, H. -J. Guntherodt, and G. N. Misevic, *Binding Strength Between Cell Adhesion Poteoglycans Measured by Atomic Force Microscopy*. Science, 1995. 267: p. 1173–1175; Jones, v. et al. *Microminiaturized Immunoassays Using Atomic Force Microscopy and Compositionally Patterned Antigen Arrays*, Analy. Chem., 1998 70(7): p. 1233–1241; and Rief, M., F. Oesterhelt, B. Heymann, and H. E. Gaub, *Single Molecule Force Spectroscopy on Polysaccharides by Atomic Force Microscopy*, Science, 1997. 275: p. 1295–1297. The above studies illustrate that it is possible to readily and directly measure the interaction between and within virtually all types of molecules by utilizing an SPM. Furthermore, recent studies have shown that it is possible to use direct force measurement to detect changes in molecular complex formation caused by the addition of a soluble molecular species. A direct force measurement may elucidate the effect of soluble molecular species on the interaction between a molecular species on an SPM probe and a surface.

Molecular Arrays

The ability to measure molecular events in patterned arrays is an emerging technology. The deposition material can be deposited on a solitary spot or in a variety of sizes and patterns on the surface. The arrays can be used to discover new compounds which may interact in a characterizable way with the deposited material. Arrays provide a large number of different test sites in a relatively small area. To form an array, one must be able to define a particular site at which a deposition sample can be placed in a defined and reproducible manner.

There are four approaches for building conventional molecular arrays known in the art. These prior art methods include 1) mechanical deposition, 2) in situ photochemical synthesis, 3) "ink jet" printing, and 4) electronically driven deposition. The size of the deposition spot (or "domain") is of particular importance when utilizing an SPM to scan for molecular recognition events. Current SPM technology only allows a scan in a defined area. Placing more domains in this defined area allows for a wider variety of molecular interaction events to be simultaneously tested.

Mechanical deposition is commonly carried out using a "pin tool" device. Typically the pin tool is a metal or similar cylindrical shaft that may be split at the end to facilitate capillary take up of liquid. Typically the pin is dipped in the source and moved to the deposition location and touched to the surface to transfer material to that domain. In one design the pin tool is loaded by passing through a circular ring that contains a film of the desired sample held in the ring by surface tension. The pin tool is washed and this process repeated. Currently, pin tool approaches are limited to spot sizes of 25 to 100 microns or larger. The spot size puts a constraint on the maximum density for the molecular deposition sites constructed in this manner. A need exists for a method that allows for molecular domains of smaller dimensions to be deposited.

In situ photochemical procedures allow for the construction of arrays of molecular species at spatial addresses in the 1–10 micron size range and larger. In situ photochemical construction can be carried out by shining a light through a mask. Photochemical synthesis occurs only at those locations receiving the light. By changing the mask at each step, a variety of chemical reactions at specific addresses can be carried out. The photochemical approach is usually used for the synthesis of a nucleic acid or a peptide array. A significant limitation of this approach is that the size of the synthetic products is constrained by the coupling efficiency at each step. Practically, this results in appreciable synthesis of only a relatively short peptide and nucleic acid specimen. In addition, it becomes increasingly improbable that a molecule will fold into a biologically relevant higher order architecture as the synthetic species becomes larger. A need exists for an alternative method for deposition of macromolecular species that will preserve the molecular formation of interest in addition to avoiding the cost of constructing the multiple masks used in this method.

Ink jet printing is an alternative method for constructing a molecular array. Ink jet printing of molecular species produces spots in the 100 micron range. This approach is only useful for printing a relatively small number of species because of the need for extensive cleaning between printing events. A key issue with ink jet printing is maintenance of the structural/functional integrity of the sample being printed. The ejection rate of the material from the printer results in shear forces that may significantly compromise sample integrity. A need exists for a method that will retain the initial structure and functional aspects of the deposition material and that will form smaller spots than are possible with the above ink jet method.

Electronic deposition is yet another method known for the construction of molecular arrays. Electronic deposition may be accomplished by the independent charging of conductive pads, causing local electrochemical events which lead to the sample deposition. This approach has been used for deposition of DNA samples by drawing the DNA to specific addresses and holding them in a capture matrix above the address. The electronic nature of the address can be used to manipulate samples at that location, for example, to locally denature DNA samples. A disadvantage of this approach is that the address density and size is limited by the dimensions of the electronic array.

A need exists for a molecular deposition technique that will allow for smaller deposition spots (domains). Smaller deposition domains allow for an array to be constructed with a greater density of domains. More domains further allow for a wider variety in the deposition material to be placed on the same array, allowing a user to search for more molecular interaction events simultaneously.

A further need exists for the ability to place these spots at a defined spatial address. Placing the domains at defined spatial addresses allows the user to know exactly what deposition material the SPM is scanning at any given time.

Furthermore, a need exists for a method to make deposition domains with large molecular weight samples that also retains the desired chemical formation. Finally, a need exists for the efficient construction of these molecule domains into an array.

Molecular Detection

All of the above examples are further limited because they require some type of labeling of the deposition sample for testing. Typical labeling schemes may include fluorescent or other tags coupled to a probe molecule. In a typical molecular event experiment, an array of known samples, for example DNA sequences, will be incubated with a solution containing a fluorescent indicator. In the DNA example this would be fluorescently or otherwise labeled nucleic acids, most often a single stranded DNA of an unknown sequence. Specific sequence elements are identified in the DNA sample by virtue of the hybridization of the label to addresses containing known sequence elements. This process has been used to screen entire ensembles of expressed genes in a given population of cells at a particular time or under a particular set of conditions. Other labeling procedures have also been employed, including RF (radio frequency) labels and magnetic labels. These methods are less frequently used, however, than the fluorescent label methods desired above. All of these labels hinder experiments with extra steps, reagents, and in some cases, risk.

Other methods for the detection of the interactions of molecules on a molecular array include inverse cyclic voltametry, capacitance or other electronic changes, radioactivity (such as with isotopes of phosphorous), and chemical reactions. In virtually all cases, some form of labeling of the probe molecule that is added to the array is required. This is a significant limitation of current arrays. A need exists for a method that does not require this extra labeling step.

Scanning Probe Microscopy

A wide variety of SPM instruments are capable of detecting optical, electronic, conductive, and other properties. One form of SPM, the atomic force microscope (AFM), is an ultra-sensitive force transduction system. In the AFM, a sharp tip is situated at the end of a flexible cantilever and scanned over a sample surface. While scanning, the cantilever is deflected by the net sum of the attractive and repulsive forces between the tip and sample. If the spring constant of the cantilever is known, the net interaction force can be accurately determined from the deflection of the cantilever. The deflection of the cantilever is usually measured by the reflection of a focused laser beam from the back of the cantilever onto a split photodiode, constituting an "optical lever" or "beam deflection" mechanism. Other methods for the detection of cantilever deflection include interferometry and piezoelectric strain gauges.

The first AFMs recorded only the vertical displacements of the cantilever. More recent methods involve resonating the tip and allowing only transient contact, or in some cases no contact at all, between it and the sample. Plots of tip displacement or resonance changes as it traverses a sample surface are used to generate topographic images. Such images have revealed the three dimensional structure of a wide variety of sample types including material, chemical, and biological specimens. Some examples of the latter include DNA, proteins, chromatin, chromosomes, ion channels, and even living cells.

In addition to its imaging capabilities, the AFM can make extremely fine force measurements. The AFM can directly sense and measure forces in the microNetwon ($10^{-6}$) to picoNewton ($10^{-12}$) range. Thus, the AFM can measure forces between molecular pairs, and even within single molecules. Moreover, the AFM can measure a wide variety of other forces and phenomena, such as magnetic fields, thermal gradients and viscoelasticity. This ability can be exploited to map force fields on a sample surface, and reveal with high resolution the location and magnitude of these fields, as in, for example, localizing complexes of interest located on a specific surface.

Direct Force Measurement

To make molecular force measurements, the AFM probe is functionalized with a molecule of interest. This bio- or chemi-active probe is then scanned across the surface of interest. The molecule tethered to the probe interacts with the corresponding molecule or atoms of interest on the surface being studied. The interactions between the molecule functionalized on the probe and the molecules or atoms on the surface create minute forces that can be measured by displacement of the probe. The measurement is typically displayed as a force vs. distance curve ("force curve").

To generate a force curve, the tip or sample is cycled through motions of vertical extension and retraction. Each cycle brings the tip into contact with the sample, then pulls the tip out of contact. The displacement of the cantilever is zero until the extension motion brings the tip into contact with the surface. Then the tip and sample are physically coupled as the extension continues. The physical coupling is the result of hard surface contact (Van der Waals interactions) between the probe and the surface. This interaction continues for the duration of the extension component of the cycle. When the cycle is reversed and the tip retracted, the physical contact is broken. If there is no attractive interaction between the tip and sample the tip separates from the sample at the same position in space at which they made contact during extension. However, if there is an adhesive interaction between the tip and sample during retraction, the cantilever will bend past its resting position and continue to bend until the restoring force of the cantilever is sufficient to rupture the adhesive force.

In the case of extendable molecular interactions, the distance between the tip and surface at which a rupture is observed corresponds to the extension length of the molecular complex. This information can be used to measure molecular lengths and to measure internal rupture forces within single molecules. In a force curve an adhesive interaction is represented by an "adhesion spike." Since the spring constant of the probe is known, the adhesive force (the unbinding force) can be precisely determined. Upon careful inspection of a typical adhesion spike, many small quantal unbinding events are frequently seen. The smallest unbinding event that can be evenly divided into the larger events can be interpreted as representing the unbinding force for a single molecular pair.

The spectra produced by these binding events will contain information about the coupling contacts holding the molecules together. Thus, it is possible to interpret the signature generated by a mechanical denaturation experiment with regard to the internal structure of the molecule. An SPM can further utilize height, friction, and elasticity measurements to detect molecular recognition events. Molecular recognition events are when one molecule interacts with another molecule or atom in, for example, an ionic bond, a hydrophobic bond, electrostatic bond, a bridge through a third molecule such as water, or a combination of these methods.

In an alternative approach, the AFM probe is oscillated at or near its resonance frequency to enable the measurement of recognizance parameters, including amplitude, frequency and phase. Changes in the amplitude, phase, and frequency parameters are extremely sensitive to variations in the interaction between the probe and the surface. If the local elasticity or viscosity of the surface changes as a result of a molecular recognition event, there is a shift in one or more of these parameters.

Others have reported using AFMs and STMs for the deposition of materials. One report is from Chad Mirkin (Northwestern University) in which he used an AFM to write nanometer scale molecule features with short alkane chains. Hong, S., J. Zhu, and C. A. Mirkin, *Multiple Ink Nanolithography: Toward A Multiple-Pen Nano-Plotter*, Science. 1999, p. 523–525. A need exists, however, for a molecular domain deposition method that is not limited to short chain length molecules. A need exists for a method for depositing longer chain length macromolecules that does not change or hinder the formation of the deposited molecule.

A need exists for an improved apparatus and method for utilization in the detection of molecular interaction events. A need exists for a method for the creation of small, submicron scale molecular domains at defined spatial addresses. This apparatus should enable the user to test for a variety of different types of events in a spatially and materially efficient manner by facilitating the deposition, exposure, and scanning of molecular domains to detect a resultant molecular interaction event. Furthermore, an apparatus is needed that enables the placement of a large number of molecular domains in a relatively small area.

SUMMARY

Figure 1:
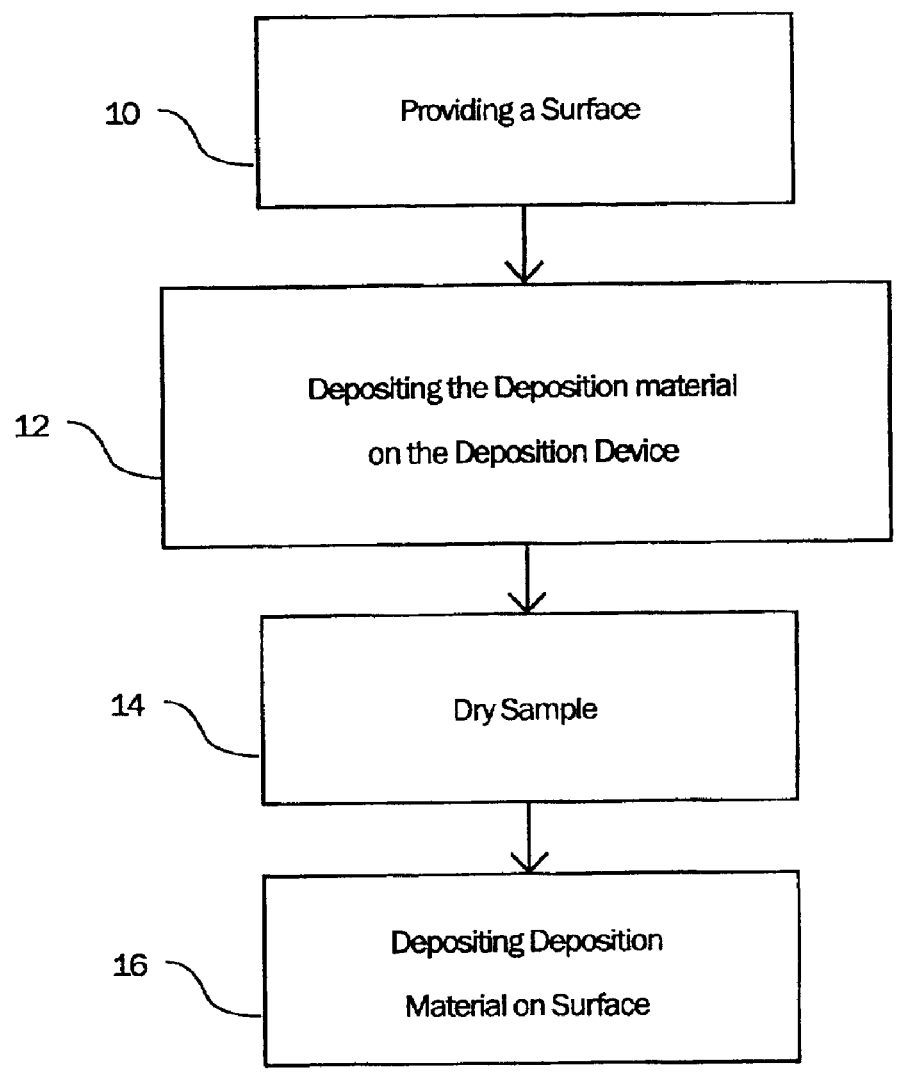
FIG. 1 is a block diagram of the method of forming a deposition domain.

A method for the construction of a molecular deposition domain on a surface, comprising, providing a surface, depositing a deposition material on a deposition device, and depositing the deposition material on the surface using said deposition device, forming a molecular deposition domain smaller than one micron in total area.

Another embodiment comprises method for constructing an array of molecular deposition domains including the steps of providing a surface, providing an at least one deposition material, depositing a first deposition material on a deposition device, depositing the first deposition material on the surface in a known position, forming a first molecular deposition domain smaller than one micron in total area, cleaning the deposition device, and repeating the above steps with an at least one other deposition material, creating an array of two or more deposition domains on said surface.

Yet another embodiment comprises a method for detecting a target sample, the method comprising, forming a molecular array on a surface, the molecular array including an at least one molecular deposition domain, said at least one molecular deposition domain smaller than one micron in total area, exposing the surface to a sample medium, the sample medium containing one or more target samples which cause a molecular interaction event in one or more of the at least one deposition domain, and scanning the surface using a scanning probe microscope to detect the occurrence of the molecular interaction event caused by the target sample.

A still further embodiment comprises a molecular array for characterizing molecular interaction events, comprising a surface, and an at least one molecular deposition domain deposited on said surface wherein the spatial address of the domain is less than one micron in area.

Another embodiment comprises a method for the processing of multiple arrays including forming an array in a substrate, the array comprising a plurality of deposition domains formed of a deposition material, exposing the array to one or more materials which contain an at least one sample molecule that causes a molecular interaction event with one or more of the deposition samples, and scanning the array utilizing a scanning probe microscope to characterize the molecular interaction events that have occurred between the target sample and the deposition material.

One object of this invention is the construction of relatively small molecular domains with large molecular species.

Another object of this invention is the construction of molecular arrays comprised of molecular domains, each containing as little as a solitary molecule.

Another object of the present invention is an apparatus and method for the creation of a molecular array comprised of one or more molecular domains, each with an area smaller than one micron.

Another object of this invention is the utilization of molecular domain arrays without having to perform a labeling step to allow for the detection of a molecular event.

Another object of this invention is a molecular deposition array that has an effective screening limit at the single molecule level.

Another object of the present invention is a method for using an AFM in a high throughput format to detect and evaluate interactions between molecules.

Another object of this invention is the placement of molecular deposition domains at a defined spatial address.

DETAILED DESCRIPTION

I. Definitions

The following are some definitions that may be helpful in understanding the description of the present invention. These are intended as general definitions and should in no way limit the scope of the present invention to those terms alone, but are put forth for a better understanding of the following description.

A. Deposition Material: This is a selected sample placed on a surface that can be recognized and/or reacted with by a target sample. The deposition material will ideally have a change inflicted upon it by one or more target samples that can be detected by later scanning with an SPM. This is the known material placed in the domain. Examples of deposition materials include, but are not limited to, biomolecules, proteins, a variety of chemicals, DNA, RNA, antibodies, or any other substance recognized by one skilled in the art which may have usefulness within the teaching of the present invention.

B. Deposition Domain: A deposition domain is a spot on a surface upon which a deposition material is placed. The domain may be of any size, shape, and pattern and may contain as little as one molecule of the deposition material. These deposition domains may alternatively be referred to as "spots" or "points." The boundary of the domain is defined by the boundary of the material placed therein.

C. Array: Alternatively referred to using the term "array," "bioarray," "molecular array," or "high density molecular array." The term array will be used to describe the one or more molecular domains deposited on the surface.

D. Target Sample: A substance with a particular affinity for one or more deposition domains. These target samples may be natural or man-made substances. The target samples may be known or unknowns present in a solution, gas, or other medium. These target samples may bind to the deposition domain or simply alter the deposition in some other cognizable way. Examples of target samples may include, but are not limited to, antibodies, drugs, nucleic acids, proteins, cellular extracts, antibodies, etc. The target medium may likewise be artificially made or, in the alternative, a biologically produced product.

E. AFM: As noted above, AFM's are a type of scanning probe microscope. The AFM is utilized in the present invention as an example of an SPM. The invention, however, is not limited for use with one specific type of AFM, but can also be incorporated for use with SPM's of various makes, models, and technological improvements.

F. Deposition Device: The deposition device of the following description is a modified AFM probe and tip. The basic probe and tip of the AFM is well known to one reasonably skilled in the art. The modified probe and tip that is the deposition device of the present invention may alternatively be referred to herein as "tip," "probe tip," or "deposition device." Other deposition devices can be substituted by one reasonably skilled in the art, including the use of a dedicated deposition device manufactured for the express purpose of sample deposition.

II. General

The apparatus and method of the present invention allows for the placement of an at least one deposition sample in an at least one molecular deposition domain forming an array. The method of creating the present invention deposition domain may result in deposition domains smaller than one micron in total area. Furthermore, this method allows the deposition of relatively large molecular species, as large as 1 kilodalton and larger, without shearing or changing the molecular formation. This array can be exposed to a sample medium that may contain a target sample, the presence of which may be ascertained and characterized by detecting molecular interaction events. The molecular interaction event detection may be performed utilizing an atomic force microscope.

The deposition domains of the present invention may be formed as small or smaller than one micron in area. The present invention allows the direct detection of molecular interaction events in the deposition domain of the array. The molecular interaction event is detected without the need for the labeling of the deposition material or of the target sample. While labeling may still be performed for use with the present invention, the present invention does not require labeling to be utilized.

The present invention utilizes a scanning probe microscope to interrogate the various deposition domains of the present invention array. As the probe is scanned over a surface the interaction between the probe and the surface is detected, recorded, and displayed. If the probe is small and kept very close to the surface, the resolution of the SPM can be very high, even on the atomic scale in some cases.

In the present embodiment, an AFM may be used as the deposition tool, but this does not exclude other types of SPM's being used in alternative embodiments. An unmodified AFM probe has a sharp point with a radius of curvature that may be between 5 and 40 nm. The method herein uses a microfabricated deposition device with an apical radius on the order of 10–50 nm. Due to the small radius of curvature of the deposition device used herein, the spot size generated by the present method can range from larger spots to as small as 0.2 microns or smaller. The difficulties with the prior art method need for labeling, such as with radioactivity, fluorescence, enzymatic labeling, etc., are also avoided.

As one reasonably skilled in the art will appreciate, the molecular material deposited by the present invention may be of almost any size and type. The following materials and methods are not intended to exclude other materials that may be compatible with the present invention, however, the present example is given for better understanding of the scope of the present invention.

Surface Preparation

Figure 2:
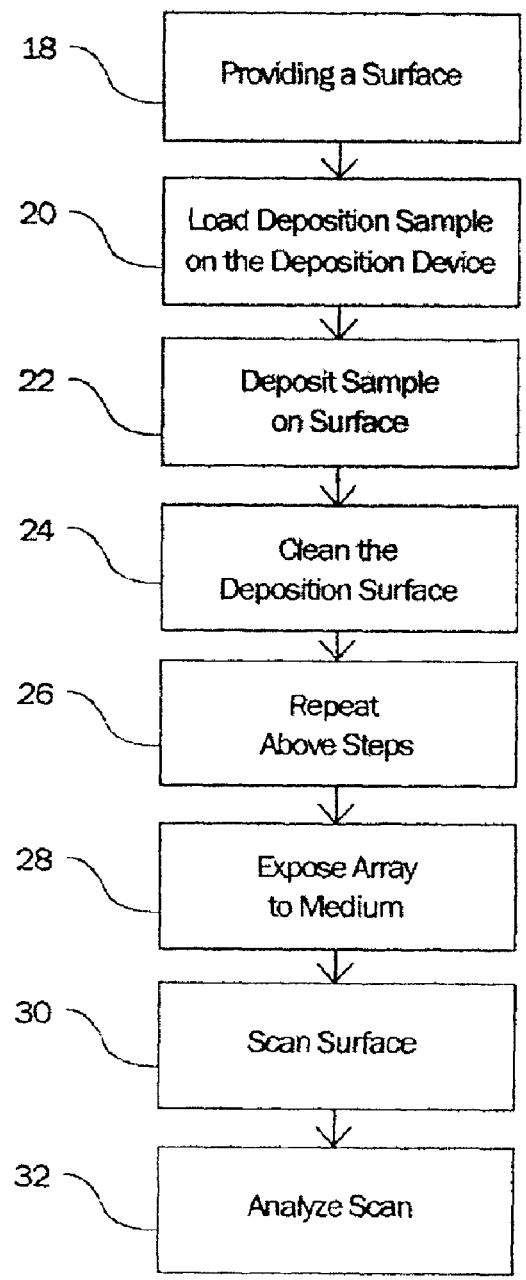
FIG. 2 is a block diagram of the method of forming an array and utilizing the same.

As shown in FIG. 1, block 10, and FIG. 2, block 18, a surface may first be provided. The deposition domains that form the array will be constructed on this surface. The surface used for the deposition of the present embodiment molecular domain should facilitate scanning by an AFM as well as facilitate the deposition of the deposition material. A surface which can accept and bind tenaciously to the deposition material may also be desired. The present embodiment utilizes a solid glass substrate. This solid glass substrate may be a glass slide well known to those reasonably skilled in the art. Other embodiments may use other substrates including, but not limited to, mica, silicon, and quartz. The present embodiment may further cover this surface with a freshly sputtered gold layer.

The ion beam sputtering of gold onto a surface is well known by those reasonably skilled in the art. Sputtering gold may produce an extremely smooth surface upon which a variety of chemistry and molecular binding may be performed. In other embodiments, the gold may be sputtered onto glass coverslips, smooth silicon, quartz or a similar flat surface. The smoothness required of the underlying substrate is a function of the sensitivity requirement of a particular test. For example, detection of a virus particle binding to antibodies on a surface requires only the smoothness of a typical glass coverslip. In contrast, detection of binding of a small ligand to a surface immobilized protein may require a supporting substrate with a surface roughness of one nanometer over an area of several microns.

In alternative embodiments, other surfaces besides that achieved by gold sputtering may be likewise utilized, such as, but not limited to, glass, Si, modified Si, (poly) tetrafluoroethylene, functionalized silanes, polystyrene, polycarbonate, polypropylene, or combinations thereof.

The gold of the present embodiment is sputtered onto the glass surface. This area of gold defines the boundary of the present embodiment array. The deposition material will be deposited in domains contained in this area.

Depositing the Deposition Sample on the Deposition Device

Figure 3:
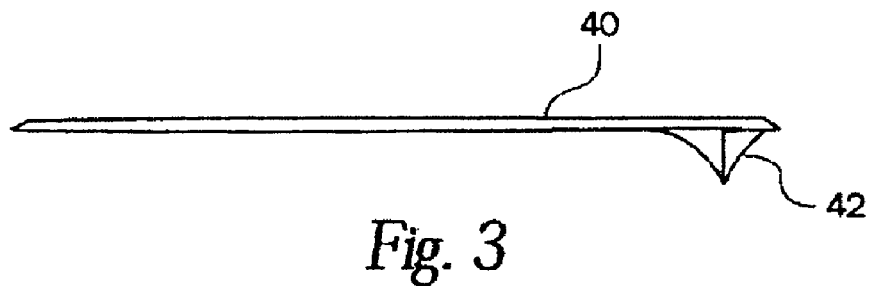
FIG. 3 is a side view of the deposition device used with the present invention.

With reference to FIG. 1 block 12, FIG. 2 block 20, and FIG. 3, the deposition of the sample on the deposition device 40 will be described. The basic shape of the deposition device 40 is shown in FIG. 3. Before the deposition material is formed into a molecular domain on the above surface, the deposition material must first be placed onto the deposition device 40. The deposition device 40 of the present embodiment may be a deposition device 40 and tip 42 commonly utilized by an AFM. The present embodiment starts with a standard silicon-nitride AFM probe under the tradename "DNP Tip" produced by Digital Instruments, Inc. These probes are generally available and well known in the art. In the present embodiment, the deposition device 40 may be first placed on the deposition instrument. A Digital Instrument, Inc., Dimension 3100 may be used in the present embodiment, controlled by a standard computer and software package known in the art.

In the present embodiment, the deposition instrument may be modified with a microsphere 52 to facilitate the loading (depositing) of the deposition material 56. While other embodiments may not utilize such a microsphere on the deposition device 40, attaching a microsphere on the deposition device 40 allows the loading of a greater amount of deposition material upon the deposition device 40, enabling a greater number of deposition domains 64 to be deposited before reloading with new material. Borosilicate glass spheres up to 25 microns or larger in diameter may be utilized in the present embodiment as the microsophere 52.

Figure 4:
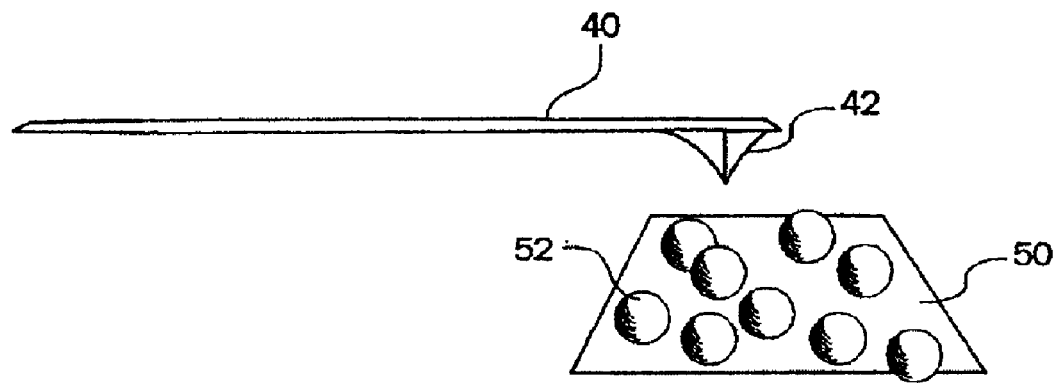
FIG. 4 is a side view of the deposition device and the microspheres of the present invention.
Figure 5:
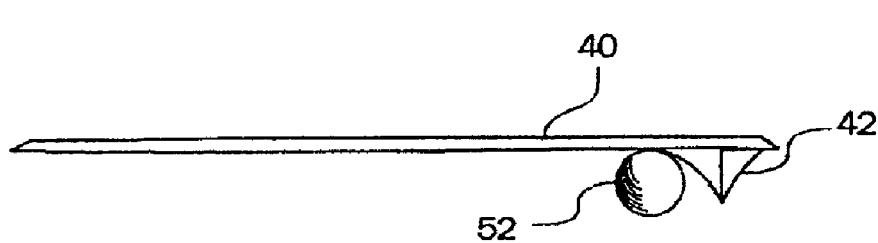
FIG. 5 is a side view of a microsphere attached to a deposition device.
Figure 6:
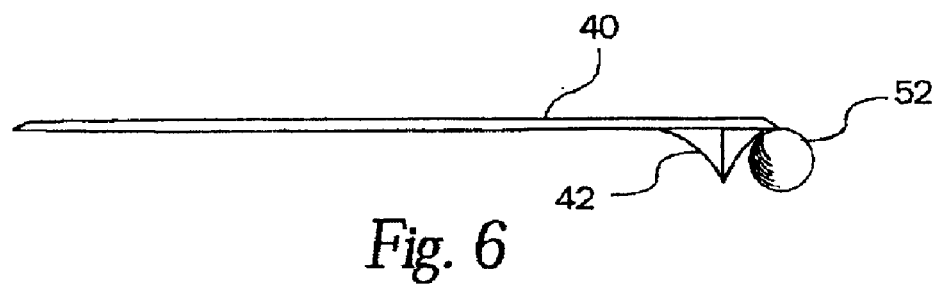
FIG. 6 is an alternative attachment of the microsphere to the deposition device.

First, a small amount of epoxy resin is placed upon a surface, usually glass. A standard ultraviolet activated epoxy resin, such as Norland Optical Adhesive #81, may be utilized, though those reasonably skilled in the art may fine other types of epoxies useful as well. The deposition device 40 is moved by the instrumentation and dipped slightly in the epoxy and withdrawn, retaining a small amount of the epoxy on the tip 42. As shown in FIG. 4, on another surface 50 are placed a number of the microspheres 52. Using the instrumentation controls, one or more of the borosilicate glass beads is touched by the end of the deposition device 40. Because of the epoxy, the microsphere 52 sticks to the end of the deposition device 40 as it is pulled away. The deposition device 40 is then exposed to ultraviolet light to set the epoxy and permanently affix the microsphere glass bead 52 to the tip 42 of the deposition device 42. As shown in FIGS. 5 and 6, the microsphere 52 may bind to the tip 42 of the deposition device 40 in various places without affecting the present invention.

The present embodiment places one microsphere 52 on the deposition device 40. This microsphere 52 allows the deposition device 40 to retain more of the material to be deposited on the probe while still allowing the creation of deposition domains 64 on the sub-micron scale. As noted above, as little as one microsphere 52 may be deposited on the tip in the above process. Furthermore, the surface of the microsphere 52 allows for alternative types of surface chemistry to be performed when, in alternative embodiments, the deposition material is being bonded to the surface.

The microspheres 52 used in the present embodiment are commercially available and well known in the art, ranging in size to smaller than 0.05 microns. With a smaller the microsphere 52, a smaller deposition domain 64 may be achieved, however less sample can be deposited on the tip at any one time, slowing down the construction of the array. Modification of the deposition device 40 may also be accomplished in a number of alternative ways, including spontaneous adsorption of molecular species, chemical derivitization of the AFM tip followed by covalent coupling of the probe molecule to the tip, or the addition of microspheres to the tip which may be coupled to molecules by standard chemistry. In additional embodiments, a laser may be used to locally heat the deposition device 40 and bond microspheres (such as polystyrene spheres) by a "spot welding" technique.

Figure 7A:
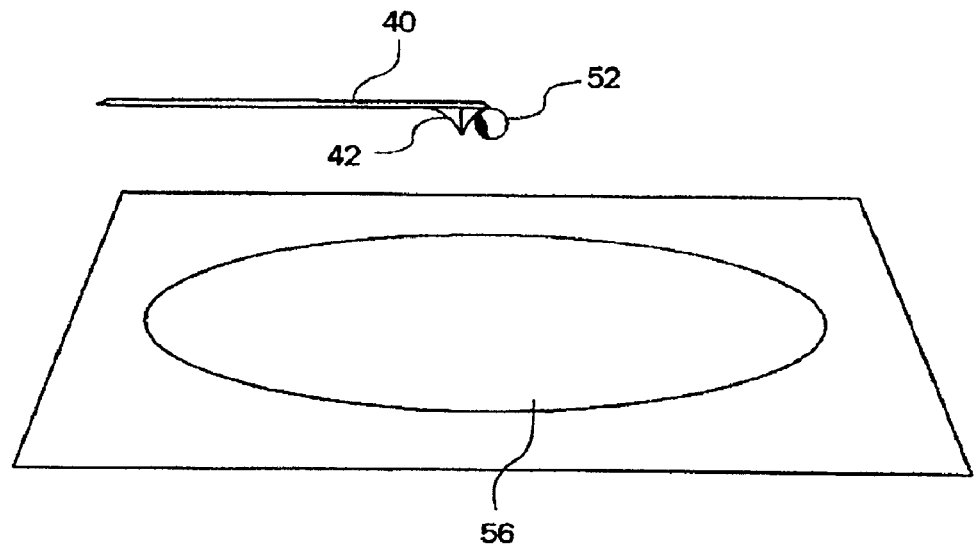
FIG. 7a is a side view of the deposition device before loading the deposition material on it.

As shown in FIG. 1 block 12, and FIG. 2 block 20, after the microsphere 52 is placed on the deposition device 40, the deposition material 56 may be loaded on the deposition device 40 by forming a capillary bridge 60. The deposition material 56 may be placed on a surface as shown in FIG. 7a. This large spot of deposition material 56 can be reused a number of times, depending on the number of domains 64 that are to be created. Though not drawn to scale, FIG. 7a shows material that may have been micro-pipetted onto a surface for loading on the deposition device 40.

In one embodiment, the deposition device 40 may be brought into direct contact with the material 56 on the surface. In alternative embodiments, the deposition device 40 and microsphere 52 may be brought into a near proximity to the deposition material 56 on the surface and achieve the same capillary action. The exact distance between the microsphere 52 and the deposition material 56 may vary and still have the formation of a capillary bridge 60. This depends on conditions like relative humidity, microsphere 52 size, contaminants, etc. In the present embodiment, this distance may vary between touching to several nanometers or more.

Figure 7B:
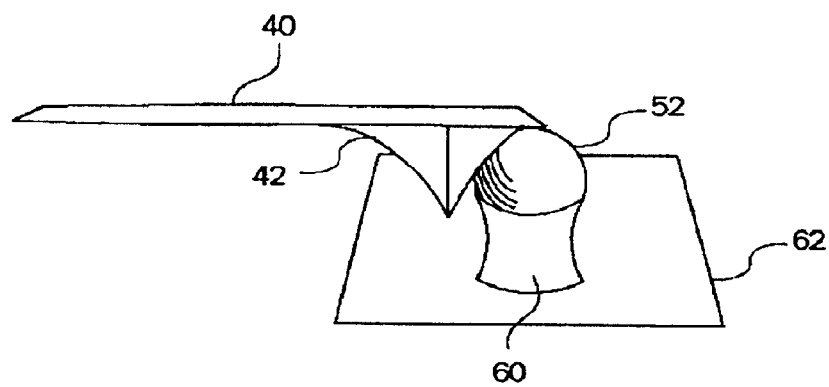
FIG. 7b is a side view of a capillary bridge between the deposition material and the microsphere during loading of the deposition material.

The capillary bridge 60, shown in FIG. 7b, may be formed by controlling the humidity by timing a blast of humid gas.

Longer bursts may result in a greater amount of material to be placed on the tip. Short bursts allow for less material to be used, but must be long enough to effectively transfer deposition material 56 from the surface 62 to the deposition device 40. The optimal parameters are determined empirically, however a typical time of exposure to the humid gas is on the order of 500 milliseconds or longer. It has also been noted that a capillary bridge 60 may be spontaneously generated when the relative humidity of the air is more than approximately 30%. In cases such as this, it may be advantageous to have a controlled dry environment or to have a stream of dry air flowing over the surface which is interrupted by the humid blast of gas which forms the capillary bridge 60. In other embodiments, this spontaneous capillary bridge 60 can be used to deposit the deposition material 56, though less control of the process may result.

In the present invention the humidity may be controlled by several methods known to those reasonably skilled in the art. The present embodiment incorporates a small tube and argon gas source which creates the bridge by rapidly increasing the level of humidity around the probe and the deposition material. The tube of the present embodiment may be a flexible polymer material, such at "Tygon" tubing, with an inner diameter of 0.5 to 1.0 cm. This material is readily available, but other materials that will not introduce contaminants into the deposition material would likewise suffice. The small tube must first be filled with water.

The water used in the present embodiment should be of a highly purified nature, such as purified water with a resistance of 18 megaohms or more. It should be free of particulates by filtration and is usually sterilized by filtration and or autoclaving. Additionally, an argon gas source may be positioned at one end of the tube and may be controlled by the action of a needle valve and solenoid.

The water is then drained from the tube, leaving a humid gas in the tube. When the humidity blast is desired, the solenoid is activated to pulse a discrete amount of humidified argon through the tube and over the probe 40, deposition material 56, and surface 62. As shown in FIG. 7b, the capillary bridge 60 may be formed between the surface 62 and the deposition device 40. The deposition device 40 is then moved away from the surface 62, leaving a small amount of the deposition material 56 on the deposition device 40, as shown in FIG. 8a.

Figure 8A:
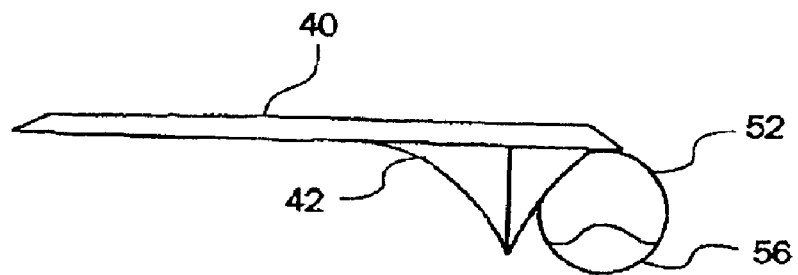
FIG. 8a is a side view of a microsphere with deposition material loaded on the microsphere.

As shown in FIG. 8a, the deposition material 56 is now on the deposition device 40. Whether the deposition material 56 adsorbs onto the microsphere's 52 surface, the pores, or some other area, may vary depending on the type of microsphere 52 and the deposition material 54. As shown in FIG. 1 block 14, the deposition material 56 may now be dried on the deposition device 40. The drying may be immediate and spontaneous due to the relatively little amount of wet material on the surface of the deposition device 40. This is, of course, dependent on the relative humidity of the surrounding air. Drying the deposition material 56 on the microsphere 56 may facilitate the deposition of the material 56 on the surface 62 as laid out in the next step. For labile samples, drying could result in inactivation, and should be avoided, but this is not the case for robust samples such as antibodies, peptides and nucleic acids.

In an alternative embodiment, the deposition tip may be loaded with the deposition material 56 by direct immersion. The tip of the probe may be immersed in a solution containing up to 50% glycerol, 0.1–5 mg/ml of the deposition sample, and a buffer-electrolyte such as Tris-HCl at pH 7.5. A small amount of the above solution may be made by standard bench chemistry techniques known to those skilled in the art. Typically 1–10 microliters are made. Because of the nature of solutions, when the probe is dipped into the solution and withdrawn a small amount of the solution will cling to the surface of the tip in a manner known to those reasonably skilled in the art. In still further embodiments, other solutions, such as 10 mM NaCl and 1 mM $MgCl_2$, phosphate buffered saline, or a sodium chloride solution, may be substituted by those reasonably skilled in the art. Alternative methods for loading the deposition material 56 on the deposition device 40 include spraying, chemically mediated adsorption and delivery, electronically mediated adsorption and delivery, and either passive or active capillary filling.

In still further embodiments, other probes may also be used, for example, AFM probes lacking a tip altogether (tipless levers), may also be used. The type of probe used may impact the spatial dimensions of the deposition domain 64 and may be influenced by the choice of the deposition sample.

Depositing the Sample On the Surface

Figure 8B:
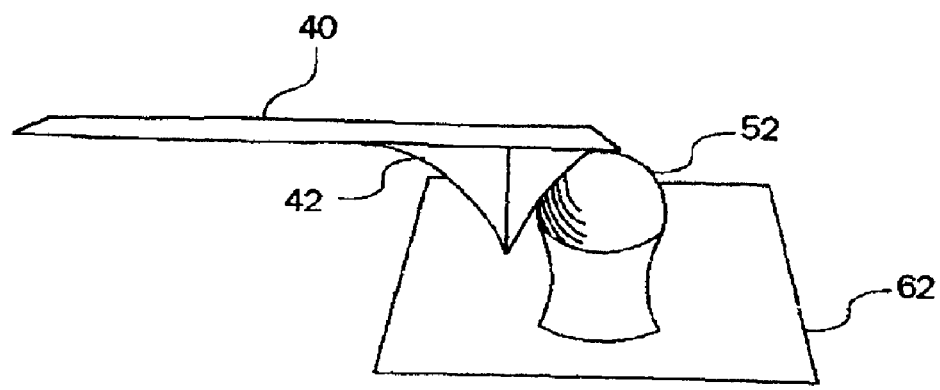
FIG. 8b is a side view of a capillary bridge between the microsphere and a surface during the deposition of a deposition domain.

The next step in creating the deposition domain 64 and array 66 is depositing the sample on the surface. See FIG. 1 block 16 and FIG. 2 block 22. Varying the humidity level surrounding the deposition device 40 and deposition material 56 may be taken advantage of to deposit the deposition material 56 onto the surface in a deposition domain 64 less than one micron in area. The capillary bridge 60 is illustrated by FIG. 8b. This step may be performed in much the same way as depositing the deposition material 56 on the deposition device 40. The degree of binding to the surface and the deposition device 40 is a function of the hydrophilicity and hydrophobicity of the two surfaces. Therefore, it may often be desirable to use deposition tools and surfaces that are free of oils and other hydrophobic contaminants to facilitate wetting of both surfaces.

Figure 9:
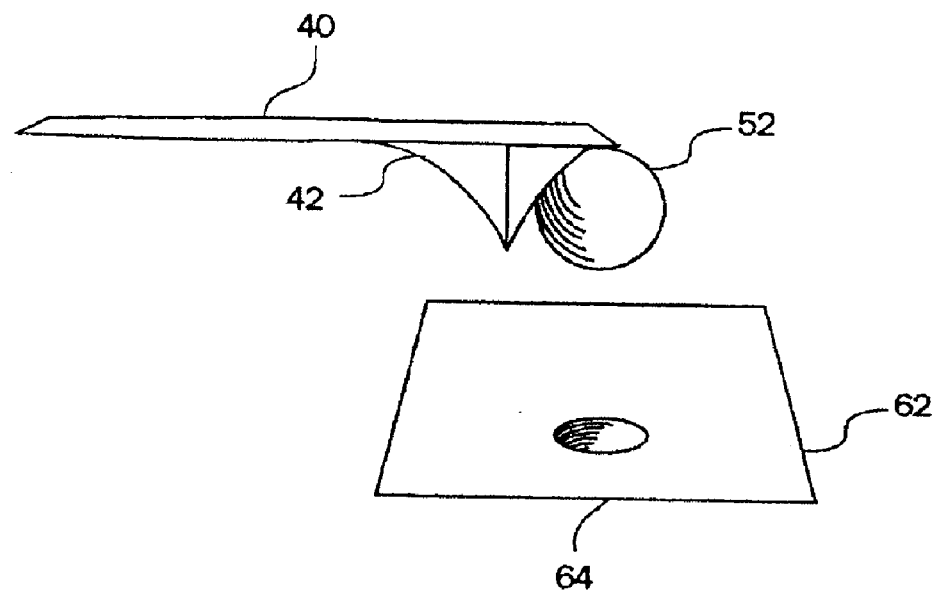
FIG. 9 is a side view of a deposition domain on an array just after the microsphere has been withdrawn.

Utilizing the AFM and the control computer and software, the deposition device 40, with the deposition material 56, may be brought into contact, or close proximity, with the deposition surface. The humid gas may then be released by activation of the solenoid. In the present embodiment the humidity is ramped up, and the capillary bridge 60 formed, for a time of approximately 400 milliseconds or less, depending on the amount of material the user wishes to deposit. The spots are on the sub-micron scale because the contact surfaces are on the order of microns or smaller and the degree of sample diffusion (which determines the final size of the deposition domain) is carefully controlled by regulating the amount and timing of the humid gas burst. When depositing the deposition sample 56 on the surface, in order to better control the length of time the capillary bridge 60 exists, a tube of dry air may be blown over the area by a solenoid in rapid succession after the humid air. This results in a very short burst of humid air, a capillary bridge 60, and then the termination of the capillary bridge 60, all in a very short time period. As illustrated in FIG. 9, when the deposition device 40 is withdrawn, and the bridge 60 severed, a very small amount of the deposition material 56 has been deposited on the surface 62 in a deposition domain 64. The transfer of large macromolecules may be achieved utilizing the burst of humid gas. As will be appreciated by one reasonably skilled in the art, the capillary bridge 60 may be broken by withdrawing the deposition device 40 or by the blast of dry air.

Because of the fine control of the deposition device 40 that may be possible with the AFM instrumentation, the exact surface spot in which the deposition takes place may be noted. Noting the surface point for each deposition domain 64 may ameliorate the detection of the molecular interaction event caused by the target sample. The pattern writing program can be one that is provided by an AFM manufacturer (e.g., the Nanolithography program provided by Digital Instruments, Inc.) or it can be created in-house. In the latter case, one example is to use a programming environment such as Lab View (National Instruments) with associated hardware to generate signal pulses which control the positioning of the deposition probe.

Figure 10:
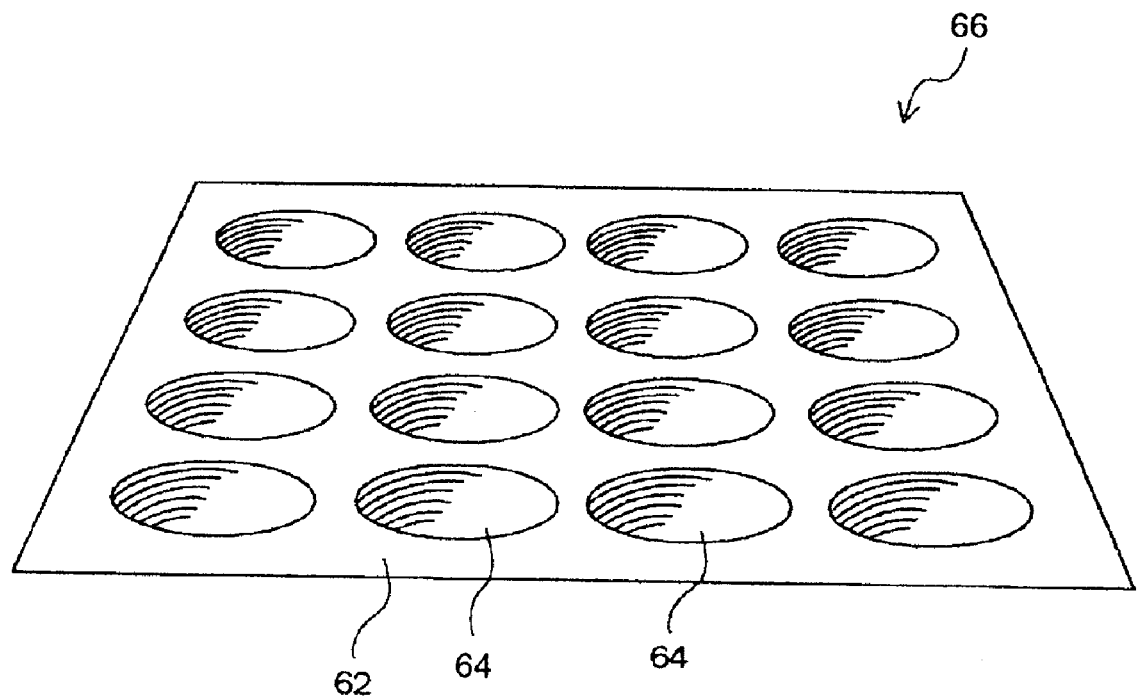
FIG. 10 is a perspective view of an array of the present invention.

The steps laid out above produce the deposition domain 64 of the present embodiment. Repeating these steps with one or more deposition materials 56, FIG. 2 block 26, produces the array 66 of the present invention. This array is shown in FIG. 10. The number and size of the deposition domains 64 may be varied depending on the desire of the user.

One advantage to the present embodiment is the small size of the deposition domain 64 produced by the method. Furthermore, because of the manner in which the array 66 is produced, the user may be able to record and track the position of each of the particular deposition domains 64. Finally, the above method allows the deposition of as little as a single macromolecule, which previous methods were unable to perform.

Once the array 66 has been formed, the user may desire to immediately utilize the array 66 on site, or may desire shipment of the array 66 for exposure to a sample medium at another location. The array 66 produced by the above steps may be ideal for shipment to a location, exposure, and return shipment for the scanning by an AFM.

Subsequent Depositions

In an alternative embodiment, the probe may be reloaded with a second deposition material 56 after one or more molecular domains are created with the first deposition material 56. FIG. 2 block 26. Using the probe with a variety of deposition materials 56 enables the creation of a number of deposition domains 64 on one surface. The different deposition materials 56 in the molecular domains that are deposited on the surface form the array 66 of the present invention. Because of the size of the molecular domain containing the deposition material 56, the molecular domains can be placed on the surface in a an ultra high density array 66, as shown in FIG. 10. In the present embodiment of this invention, the pitch (the distance from the center of one domain to the center of the next domain) of the molecular domains may be as small or smaller than one micron. The array 66 produced with these small molecular domains may be easily scanned by the AFM array 66 after the array 66 is exposed to the sample medium containing the target sample in the next step. Furthermore, the small sized array 66 requires exposure to a smaller amount of the sample medium of the next step, conserving both the deposition material 56 and the medium material.

The number of times the probe may be reloaded in this alternative embodiment may be only limited by the surface size and the number of samples the user desires to deposit. As will be appreciated by those skilled in the art, this ultra high density array 66 presents a unique advantage.

Cleaning the Probe

Before the probe is reloaded with subsequent deposition samples, the probe must be cleaned. FIG. 2 block 24. The probe of the present embodiment AFM may be cleaned in several ways. In the present embodiment, the very tip of the probe is immersed in a small aliquot of a cleaning solution. The present embodiment cleaning step utilizes pure water as the solution. A few microliters of water is pipetted onto a surface and, using the instrumentation's piezo device (which is utilized to help the AFM scan surfaces), the tip is oscillated at up to 1000 Hz or more. Resonating the probe at 1000 hertz will effectively sonicate the tip, helping to effectuate reusing the tip to deposit other deposition materials 56.

Exposing the Array To a Sample Medium

Once a high density array 66 is formed by the present invention, the array 66 may be exposed to a sample medium. FIG. 2 block 28. The sample medium may contain a target sample that the user has placed therein. In other types of experiments, the user may be looking for the presence of an unknown target sample, utilizing the array 66 of the present invention to test for its presence. The usefulness of such arrays 66 are well known to those reasonably skilled in the art The array 66 may be dipped in a solution or exposed to a gas. The solution may include, but is not limited to, waste water, biological materials, organic or inorganic user prepared solutions, etc. The exposure time of the array 66 to the medium depends on what types of molecular interaction events the user may be studying. The target sample tested for should ideally cause a readable molecular change in one or more of the deposition materials 56 of the molecular domains placed on the array 66. These molecular changes may include binding, changes in stereochemical orientation in morphology, dimensional changes in all directions, changes in elasticity, compressibility, or frictional coefficient, etc. The above changes are what the AFM scans and reads in the next step of the present embodiment.

Molecular Event Detection

After the molecular deposition array 66 is exposed to the test medium, it may be scanned by the AFM. See FIG. 2 block 30. Use of an AFM in this manner to characterize a material deposited on a surface is well known to those reasonably skilled in the art. The present embodiment may utilize one scan for every deposition domain 64 of the array 66 to look for changes in the recorded features of the domains. Furthermore, the AFM may look at specific portions of the array 66 using site locators. As will be appreciated by one skilled in the art, various methods may be used to undertake the scanning of the array 66 of the present invention.

Figure 11:
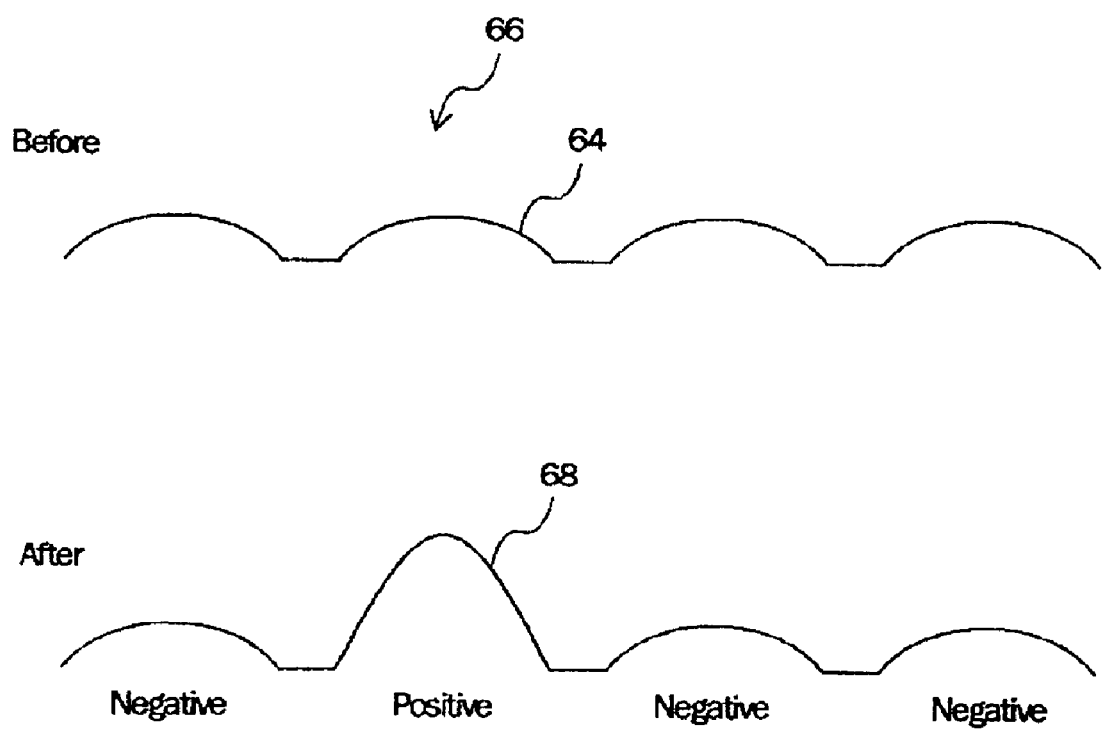
FIG. 11 is an outline view of an example scan of an array after exposure to a target medium.

After the scan is taken, the scan must be analyzed. FIG. 2, block 32. The present embodiment utilizes the detection of changes in height at defined spatial addresses, as described by Jones et al., supra. As shown in FIG. 11, height changes only occur at those addresses containing deposition material 56 to which the target sample is capable of binding. Since the identity of the molecules at each of the sample addresses is known, this process immediately identifies those deposition materials 56 capable of binding to the target sample. In FIG. 11, point 66 shows the normal height of the deposition domain 64 as scanned by the AFM. Point 68 shows how the AFM will recognize some feature that the molecular interaction event has affected in the deposition domain 64.

In addition, the AFM can measure whether new materials have bonded to the deposition material 56 by testing for changes in shape (morphology) as well as changes in local mechanical properties (friction, elasticity, compressibility, etc.) by virtue of changes in the interaction between the probe and the surface. The typical parameters detected by an AFM include height, torsion, frequency (the oscillation frequency of the AFM probe in AC modes of operation), phase (the phase shift between the driving signal and the cantilever oscillation in AC modes) and amplitude (the amplitude of the oscillating cantilever in AC modes of operation).

The AFM scan may also be used to tell when the probe is interacting with different forces of adhesion (friction) at different domains on the surface. This interaction force is a consequence of the interaction between the molecules on the probe and on the surface. When there is a specific interaction, the force value is typically higher than for non-specific interactions, although this may not be universally true (since some non-specific interactions can be very strong). Therefore, it may be useful to include both known positive and negative control domains in the scan area to help distinguish between specific and non-specific force interactions. The target sample may affect the deposition material 56 that can be read by this scanning technique. A still further embodiment may directly measure the interaction forces between a molecular probe coupled to the AFM tip and the surface. The direct measurement of molecular unbonding forces has been well described in the art in addition to measuring changes in the elasticity.

In the screening methods described above, once it has been established that a molecular binding event has occurred, changes in the degree of binding upon introduction of additional sample molecules may also be analyzed. The potential for a third molecular species to enhance or inhibit a defined molecular interaction is of utility in locating new drugs and other important effectors of defined molecular interactions.

In the above examples an AFM is used for illustration purposes. The type of deposition instrumentation incorporated into the present invention is not limited to AFM's, or other types of SPM's. In one alternative embodiment, a dedicated deposition instrument may be used which may provide for extremely accurate control of the deposition probe. In this alternative embodiment, a DC stepper motor and a piezoelectric motion control device may be incorporated for sample and probe control. In still further embodiments, a force feedback system may be included to minimize the force exerted between the deposition tool and the surface.

One advantage to the present invention is the elimination of the labeling step required in other array 66 techniques. Radioactive and fluorescent labeling may be cost prohibitive and complex. The present invention eliminates the need for the labeling of molecular deposition domains 64 in an array 66.

Another advantage to the present invention is the creation of molecular domains in an array 66 wherein each domain has a deposition area of less than one micron. Since the size of each domain is extremely small, a large number of domains may be placed in a small area, requiring less materials, a smaller medium sample for exposure, and the ability to perform a quicker scan.

Another advantage to the present invention array 66 is the ability to quickly scan for multiple molecular events in a reasonably short period of time.

III. Alternative Deposition Examples

The following are a few of the variations in the deposition method and array 66 apparatus that may be used within the scope of the present invention. These examples are given to show the scope and versatility of the present invention and are not intended to limit the invention to only those examples given herein. In each of these examples, the deposition material 56 may be deposited on the deposition device 40 and then to the surface utilizing the method described above, however the surface may be coated with other materials that will react in some way with the deposition material 56, to bind the latter to the surface in the deposition domain 64.

A. Surface Modification

One alternative embodiment for the covalent tethering of biomaterials to a surface for use in the present invention may be to use a chemically reactive surface. Such surfaces include, but are not limited to, surfaces with terminal succinimide groups, aldehyde groups, carboxyl groups, vinyl groups, and photoactivatable aryl azide groups. Other surfaces are known to those reasonably skilled in the art. Biomaterials may include primary amines and a catalyst such as the carbodiimide EDAC (1-ethyl-3-[3-dimethylaminopropyl]carbodiimide). Furthermore, the spontaneous coupling of succinimide, or in the alternative, aldehyde surface groups, to primary amines at a physiological pH may be incorporated for attaching molecules to the surface. In still another embodiment, photoactivatable surfaces, such as those containing aryl azides, may be utilized. These photoactivatable surfaces form highly reactive nitrenes that react promiscuously with a variety of chemical groups upon ultraviolet activation. Placing the deposition sample on the surface and then activating the material can create deposition domains 64 in spots or patterns, limited only by the light source activated.

Another embodiment for the tenacious and controlled binding of biomaterials to surfaces is to exploit the strong interactions between various biochemical moieties. For example, histidine binds tightly to nickel. Therefore, both nucleic acid and protein biomaterials may be modified using recombinant methods to produce runs of histidine, usually 6 to 10 amino acids long. This His-rich domain then allows these molecules to bind tightly to nickel coated surfaces. Alternatively, sulfhydryl groups can be introduced into protein and nucleic acid biomaterials, or preexist there, and can be used to bind the biomaterials to gold surfaces by virtue of extremely strong gold-sulfur interaction. It is well documented that gold binds to sulfur with a binding force comparable to that of a covalent bond. Therefore, gold-sulfur interactions have been widely exploited to tether molecules to surfaces. Jones, V. W., J. R. Kenseth, M. D. Porter, C. L. Mosher, and E. Henderson, Microminiaturized Immunoassays Using Atomic Force Microscopy and Compositionally Patterned Antigen Arrays 66, Anal Chem. 1998, p. 1233–41.

B. APTES

In this alternative embodiment, the surface may be treated with APTES (aminopropyl triethoxy silane). The APTES placed on the surface may present positively charged amino groups that can bind tightly to a negative charge. Materials such as DNA and RNA containing negatively charged groups may therefore bond to the surface after the APTES treatment. The details of the adsorption mechanism involved in this spontaneous attachment are not well defined. Therefore, in alternative embodiments, it may be advantageous to deposit biomaterials onto surfaces that can be covalently or otherwise tenaciously coupled to the target sample. DNA and RNA bind through interaction between their negative net charge and the net positive charge of the APTES surface.

C. Photochemical Sample Deposition

In this alternative embodiment, glass surfaces may be modified sequentially by two compounds, aminopropyltriethoxysilane (APTES) and N-5-azido-2-nitrobenzoyloxysuccinimide (ANB-NOS). The glass may first be treated with APTES to generate a surface with protruding amino groups ($NH_2$). These groups may be then reacted with the succinimide moiety of ANB-NOS in the dark. These steps produce a surface with protruding nitrobenzene groups. The photosensitive surface may be then reacted with the first deposition material 56 in the dark, then a focused light source, like a laser, may be used to illuminate a portion of the surface. These acts result in localized covalent binding of the first deposition material 56 to the surface. The deposition material 56 not bonded to the surface may then be washed away and second deposition material 56 added by repeating the process. Reiteration of this process results in the creation of a biomolecular array 66 with address dimensions in the 1 micron size range. A limitation of this deposition method is that the sample size is dependent on the size of the illuminating light field.

A variation of the above embodiment may be to utilize the deposition device 40 and humidity ramping deposition technique described to place various molecular species at defined locations in the dark. After construction of the desired array 66, the entire surface is exposed to light, thereby cross linking the molecular species at discrete spatial domains. This process may overcome the spatial limitation imposed by use of a far field laser or other type of light beam.

D. Photocoupling

In this embodiment a near field scanning optical microscope (NSOM) may be used to supply the light energy necessary to accomplish photocoupling of the sample molecule to a surface at a defined spatial address. The NSOM may overcome the diffraction limit which constrains the address size created by far field photocoupling as described in Example 2. The photoactive surface is prepared as described in Example II. The first molecule to be coupled is added to the surface and subjected to a nearfield evanescent wave emanating from the aperture of the NSOM. The evanescent wave energy may then activate the photosensitive surface and result in coupling of the sample molecules to a spatial address in the 10 to 100 nm size range. The first sample molecule is washed away and the process repeated with a second sample molecule. Reiteration of this process may result in the production of an array 66 of sample molecules coupled at spatial addresses with submicron dimensions.

An alternative approach may be to utilize both the sample manipulation and near field light delivery capabilities of the NSOM. In this approach, the NSOM probe may be first loaded with a molecular species as described in Example I. Then the same probe is used to provide the light energy to couple the molecule to the surface. The probe may then be washed and reused to create a spatial array 66 of molecular species covalently coupled to defined domains.

One advantage of coupling the deposition material 56 to the surface may be that the molecule may remain attached at a defined spatial domain even under stringent wash and manipulation conditions. Moreover, by coupling the molecule, the orientation of the molecules on the surface may be controlled by the careful selection of a tethering method.

Yet another advantage to coupling the molecule is that by controlling the coupling chemistry, the minimization of the chances of surface induced molecular denaturation may be achieved. Coupling the molecules to the surface may be especially advantageous when depositing biomolecules.

The information and examples described herein are for illustrative purposes and are not meant to exclude any derivations or alternative methods that are within the conceptual context of the invention. It is contemplated that various deviations can be made to this embodiment without deviating from the scope of the present invention. Accordingly, it is intended that the scope of the present invention be dictated by the appended claims rather than by the foregoing description of this embodiment.

All publications cited in this application are incorporated by reference in their entirety for all purposes.

What is claimed is:

1. A method for the construction of a molecular deposition domain on a surface, comprising:
    (a) providing a surface;
    (b) depositing a deposition material on a deposition device, wherein the deposition material comprises a biomolecule;
    (c) depositing the deposition material on the surface using said deposition device, forming a molecular deposition domain smaller than one micron squared.

2. A method for the construction of a molecular deposition domain on a surface, comprising:
    (a) providing a surface;
    (b) placing a deposition device in contact with or near proximity to a deposition material to be deposited;
    (c) exposing the deposition device and the deposition material to a humid gas so that a capillary bridge is formed between the deposition device and the deposition material;
    (d) retracting the deposition device, retaining a portion of the deposition material on the deposition device;
    (e) depositing the deposition material on the surface using said deposition device, forming a molecular deposition domain smaller than one micron squared.

3. The method of claim 2 further comprising drying the deposition material on the deposition device of step (d).

4. The method of claim 1 wherein depositing the deposition material on the deposition device comprises
    contacting the deposition device with the deposition material retaining a portion of the deposition material on the deposition device , and
    drying the deposition material on the deposition device.

5. The method of claim 1 wherein depositing the deposition material on said surface further comprises:
    (d) placing the deposition device in a position adjacent to the surface;
    (e) exposing the deposition device and the surface to a humid gas so that a capillary bridge is formed between the deposition device and the surface;
    (f) withdrawing the deposition device from the position adjacent to the surface, leaving a portion of the deposition material on the surface in a deposition domain smaller than one micron squared.

6. The method of claim 5 wherein withdrawing the device further comprises exposing the deposition domain, the surface, and the deposition device to a dry gas to sever the capillary bridge.

7. The method of claim 1 wherein depositing the deposition material on said surface further comprises:
    (a) touching the deposition device with the deposition material on it to the surface;
    (b) exposing the deposition device and surface to a humid gas so that a capillary bridge forms between the deposition device and the surface;
    (c) retracting the deposition device from the surface leaving a deposition domain on the surface.

8. The method of claim 7 wherein withdrawing the device further comprises exposing the deposition domain, the surface, and the deposition device to a dry gas to sever the capillary bridge.

9. A method for the construction of a molecular deposition domain on a surface, comprising:

(a) providing a surface wherein the surface comprises a sputtered layer of gold;

(b) depositing a deposition material on a deposition device;

(c) depositing the deposition material on the surface using said deposition device, forming a molecular deposition domain smaller than one micron squared.

10. The method of claim 1 wherein providing the surface further comprises chemically modifying said surface with a reactive material.

11. The method in claim 1 wherein the molecular deposition domain is a line.

12. The method in claim 1 wherein the molecular deposition domain is a spot.

13. The method in claim 1 wherein the molecular deposition domain is an irregular shape.

14. The method in claim 1 wherein the molecular deposition domain is a regular shape.

15. The method of claim 1 wherein said surface is chosen from one or more of the group consisting of a hydrophobic surface, a hydrophilic surface, and a chemically modified surface.

16. The method of claim 1 wherein said surface is chosen from one or more of the group consisting of a polymer and a metal.

17. The method of claim 1 wherein preparing said surface further comprises modifying the surface with one or more of the group consisting of an amino group and a carboxyl group.

18. The method of claim 1 wherein said surface is physically modified.

19. The method of claim 1 wherein said surface is physically modified with a metal.

20. The method of claim 1 wherein said surface is chosen from one or more of the group consisting of mica, silicon, glass, and quartz.

21. The method of claim 1 wherein said deposition material is chosen from one or more of the group consisting of proteins, antibodies, nucleic acids, DNA, and RNA.

22. The method of claim 1 in which said deposition material comprises long chain molecules.

23. The method of claim 1 wherein the surface comprises a chemically modified surface and wherein the deposited deposition material is immobilized.

24. The method of claim 23 wherein the immobilized deposition material is chosen from one or more of the group consisting of a nucleic acids, a proteins, a lipids, and a sugar.

25. The method of claim 23 wherein the deposition device is a scanning probe microscope probe.

26. A method for the construction of a molecular deposition domain on a surface, comprising:

(a) providing a surface;

(b) depositing a deposition material on a deposition device wherein the deposition device further comprises an attached microsphere;

(c) depositing the deposition material on the surface using the deposition device, forming a molecular deposition domain.

27. The method of claim 26 wherein the microsphere is up to 25 microns in diameter.

28. The method of claim 26 wherein the microsphere is larger than 25 microns in diameter.

29. The method of claim 26 wherein the microsphere comprises a non-porous material.

30. The method of claim 26 in which the microsphere comprises a porous material.

31. The method of claim 26 in which the microsphere comprises glass.

32. The method of claim 1 wherein the deposition device is controlled by a computer.

33. The method of claim 1 wherein depositing the deposition material on the deposition device further comprises regulating the humidity surrounding the deposition device and the surface.

34. The method of claim 1 wherein the surface of step (a) comprises activated chemical groups.

35. The method of claim 34 wherein the chemical groups are activated from an energy source in the far field.

36. The method of claim 34 wherein the chemical groups are activated from an energy source in the near field.

37. The method of claim 34 wherein the surface is photosensitive.

38. A method for constructing an array of molecular deposition domains comprising:

(a) providing a surface;

(b) providing an at least one deposition material;

(c) depositing a first deposition material on a deposition device;

(d) depositing the first deposition material on the surface in a known position, forming a first molecular deposition domain smaller than one micron squared in total area;

(e) cleaning the deposition device;

(f) repeating the above steps to form an at least one other deposition domain, creating an array of two or more deposition domains on said surface.

39. The method of claim 38 wherein cleaning the deposition device comprises sonication.

40. The method of claim 1, wherein the biomolecule comprises histidine and wherein the surface comprises nickel.

41. The method of claim 1, wherein the biomolecule comprises a sulfhydryl group and wherein the surface comprises gold.

42. The method of claim 1 further comprising drying the deposition material on the deposition device of step (b).

43. The method of claim 26, wherein the deposition domain is smaller than one micron squared.

44. The method of claim 26, wherein the deposition material comprises a biomolecule.

* * * * *

(12) EX PARTE REEXAMINATION CERTIFICATE (6322nd)
United States Patent
Henderson et al.

(10) Number: US 6,998,228 C1
(45) Certificate Issued: Jul. 22, 2008

(54) METHOD AND APPARATUS FOR SOLID STATE MOLECULAR ANALYSIS

(75) Inventors: Eric Henderson, Ames, IA (US); Curtis Mosher, Ames, IA (US); Michael P. Lynch, Ames, IA (US)

(73) Assignee: Bioforce Nanosciences, Inc., Ames, IA (US)

Reexamination Request:
No. 90/008,384, Feb. 8, 2007

Reexamination Certificate for:
Patent No.: 6,998,228
Issued: Feb. 14, 2006
Appl. No.: 10/179,102
Filed: Jun. 25, 2002

Related U.S. Application Data

(62) Division of application No. 09/574,519, filed on May 18, 2000, now Pat. No. 6,573,369.
(60) Provisional application No. 60/135,290, filed on May 21, 1999.

(51) Int. Cl.
*C12Q 1/68* (2006.01)

(52) U.S. Cl. .................. 435/4; 435/6; 435/7.1; 977/858

(58) Field of Classification Search .............. None
See application file for complete search history.

(56) References Cited

U.S. PATENT DOCUMENTS

| | | | |
|---|---|---|---|
| 5,002,582 A | 3/1991 | Guire et al. |
| 5,807,522 A | 9/1998 | Brown et al. |
| 5,861,242 A | 1/1999 | Chee et al. |
| 6,110,691 A | 8/2000 | Wang et al. |
| 6,406,921 B1 | 6/2002 | Wagner et al. |
| 6,410,231 B1 | 6/2002 | Arnold et al. |
| 6,635,311 B1 | 10/2003 | Mirkin et al. |
| 6,716,578 B1 | 4/2004 | Henderson et al. |
| 2001/0055754 A1 | 12/2001 | McGrath et al. |

OTHER PUBLICATIONS

U.S. Appl. No. 60/115,133, filed Jan. 7, 1999, Mirkin et al.
U.S. Appl. No. 60/123,362, filed Mar. 8, 1999, Henderson et al.
U.S. Appl. No. 60/157,633, filed Oct. 4, 1999, Mirkin et al.
Piner et al., "Dip–pen nanolithography," *Science* 283, 661–663, 1999.
Jones et al., "Microminiaturized immunoassays using atomic force microscopy and compositionally patterned antigen arrays," *Anal. Chem.*, vol. 70 (1998), pp. 1233–1241.
Shaiu, W. et al. "Atomic force microscopy of oriented linear DNA molecules labeled with 5nmgold spheres", Nucleic Acids Res., vol. 21, No. 1, pp. 99–103 (1993).
Marsch, T., et al., "A new DNA nanostructure, the G–wire, imaged by scanning probe microscopy", Nucleic Acids Res., vol. 23, No. 4, pp. 696–700 (1995).
Fritz, M., et al., "Imaging Globular and Filamentous Proteins in Physiological Buffer Soutions with Tapping Mode Atomic Force Microscopy", Langmuir, vol. 11, pp. 3529–3535 (1995).

*Primary Examiner*—Padmashri Ponnaluri

(57) ABSTRACT

The invention is a method for the formation and analysis of novel miniature deposition domains. These deposition domains are placed on a surface to form a molecular array. The molecular array is scanned with an AFM to analyze molecular recognition events and the effect of introduced agents on defined molecular interactions. This approach can be carried out in a high throughput format, allowing rapid screening of thousands of molecular species in a solid state array. The procedures described here have the added benefit of allowing the measurement of changes in molecular binding events resulting from changes in the analysis environment or introduction of additional effector molecules to the assay system. The processes described herein are extremely useful in the search for compounds such as new drugs for treatment of undesirable physiological conditions. The method and apparatus of the present invention does not require the labeling of the deposition material or the target sample and may also be used to deposit large size molecules without harming the same.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 26–31, 43 and 44 is confirmed.

Claims 6–8 and 39 are cancelled.

Claims 1, 2, 5, 9 and 38 are determined to be patentable as amended.

Claims 3, 4, 10–25, 32–37 and 40–42, dependent on an amended claim, are determined to be patentable.

1. A method for the construction of a molecular deposition domain on a surface, comprising:
   (a) providing a surface;
   (b) depositing a deposition material on a deposition device, wherein the deposition material comprises a biomolecule;
   (c) [depositing the deposition material on the surface using said deposition device] *touching the deposition device with the deposition material on it to the surface;*
   (d) *exposing the deposition device and surface to a blast of humid gas so that a capillary bridge forms between the deposition device and the surface; and*
   (e) *retracting the deposition device from the surface,* forming a molecular deposition domain smaller than one micron squared *on the surface, wherein retracting the deposition device includes exposing the deposition domain, the surface, and the deposition device to a blast of dry gas to sever the capillary bridge.*

2. A method for the construction of a molecular deposition domain on a surface, comprising:
   (a) providing a surface *and a deposition device, the deposition device comprising a microsphere attached thereto*;
   (b) placing [a] *the* deposition device in contact with or near proximity to a deposition material to be deposited;
   (c) exposing the deposition device and the deposition material to a *blast of* humid gas so that a capillary bridge is formed between the deposition device and the deposition material;
   (d) retracting the deposition device, retaining a portion of the deposition material on the deposition device;
   (e) depositing the deposition material on the surface using said deposition device, forming a molecular deposition domain smaller than one micron squared.

5. [The] *A* method of [claim 1 wherein depositing the deposition material on said surface further comprises] *construction of a molecular deposition domain on a surface, comprising*:
   (a) *providing a surface;*
   (b) *depositing a deposition material comprising a biomolecule on a deposition device;*
   [(d)] (c) placing the deposition in a position adjacent to the surface;
   [(e)] (d) exposing the deposition device and the surface to a *blast of* humid gas so that a capillary bridge is formed between the deposition device and the surface; *and*
   [(f)] (e) withdrawing the deposition device from the position adjacent to the surface, leaving a portion of the deposition material on the surface in a deposition domain smaller than one micron squared, *wherein withdrawing the deposition device includes exposing the deposition domain, the surface, and the deposition device to a blast of dry gas to sever the capillary bridge.*

9. A method for the construction of a molecular deposition domain on a surface, comprising:
   (a) providing a surface wherein the surface comprises a sputtered layer of gold;
   (b) depositing a deposition material on a deposition device, *the deposition device comprising a microsphere attached thereto*;
   (c) depositing the deposition material on the surface using said deposition device, forming a molecular deposition domain smaller than one micron squared.

38. A method for constructing an array of molecular deposition domains comprising:
   (a) providing a surface;
   (b) providing an at least one deposition material;
   (c) depositing a first deposition material on a deposition device;
   (d) depositing the first deposition material on the surface in a known position, forming a first molecular deposition domain smaller than one micron squared in total area;
   (e) cleaning the deposition device *by sonication*;
   (f) repeating the above steps to form an at least one other deposition domain, creating an array of two or more deposition domains on said surface.

* * * * *